United States Patent
Wong et al.

(10) Patent No.: US 12,163,077 B2
(45) Date of Patent: Dec. 10, 2024

(54) ULTRABRIGHT LUMINESCENT LANTHANIDE NANOPARTICLES COMPRISING TERBIUM, WITH LONGER EXCITED-STATE LIFETIME

(71) Applicants: Université De Strasbourg, Strasbourg (FR); Centre National De La Recherche Scientifique, Paris (FR); Université Paris Saclay, Saint Aubin (FR); Hong Kong Baptist University, Kowloon (HK)

(72) Inventors: Ka-Leung Wong, Kawloon (HK); Joan Goetz, Strasbourg (FR); Loïc Charbonniere, Weyersheim (FR); Niko Hildebrandt, Orsay (FR); Aline Nonat, Eckbolsheim (FR); Cyrille Charpentier, Strasbourg (FR); Marcelina Cardoso Dos Santos, Gif-sur-Yvette (FR); Vjona Cifliku, Gif-sur-Yvette (FR)

(73) Assignees: UNIVERSITE DE STRASBOURG, Strasbourg (FR); CENTRE NATIONAL DE LA RECHERCHE SCIENTIFIQUE, Paris (FR); UNIVERSITE PARIS SACLAY, Saint Aubin (FR); HONG KONG BAPTIST UNIVERSITY, Kowloon (HK)

( * ) Notice: Subject to any disclaimer, the term of this patent is extended or adjusted under 35 U.S.C. 154(b) by 943 days.

(21) Appl. No.: 17/255,211

(22) PCT Filed: Jul. 4, 2019

(86) PCT No.: PCT/EP2019/067959
§ 371 (c)(1),
(2) Date: Dec. 22, 2020

(87) PCT Pub. No.: WO2020/007966
PCT Pub. Date: Jan. 9, 2020

(65) Prior Publication Data
US 2021/0253950 A1 Aug. 19, 2021

(30) Foreign Application Priority Data
Jul. 5, 2018 (EP) .................................. 18305890

(51) Int. Cl.
*C09K 11/77* (2006.01)
*C09K 11/02* (2006.01)
(Continued)

(52) U.S. Cl.
CPC .......... *C09K 11/779* (2013.01); *C09K 11/025* (2013.01); *B82Y 5/00* (2013.01);
(Continued)

(58) Field of Classification Search
CPC ... C09K 11/025; C09K 11/77; C09K 11/7743; C09K 11/7783; C09K 11/779; B82Y 5/00; B82Y 20/00; B82Y 30/00; B82Y 40/00
See application file for complete search history.

(56) References Cited

U.S. PATENT DOCUMENTS 6,159,686 A * 12/2000 Kardos ................ G01N 33/588
435/7.1

* cited by examiner

*Primary Examiner* — Matthew E. Hoban
*Assistant Examiner* — Lynne Edmondson
(74) *Attorney, Agent, or Firm* — Birch, Stewart, Kolasch & Birch, LLP

(57) ABSTRACT

The invention provides luminescent lanthanide nanoparticles having simultaneously an improved brightness and an
(Continued)

increased lifetime of the excited-state. These nanoparticles comprise terbium ions and ions of a second lanthanide, preferentially europium, and are coated with molecules of chromophore ligand bonded to the surface of the nanoparticle. The ligand is an organic molecule comprising at least one chromophore radical of formula (I) or of formula (II): wherein R is selected from H, CN group or COOH group. The phosphorescence excited-state lifetime is improved by energy transfer from surface terbium ions to core ions of the second lanthanide. The nanoparticle may further comprise a carrier molecule of analytical interest covalently attached to at least one ligand molecule.

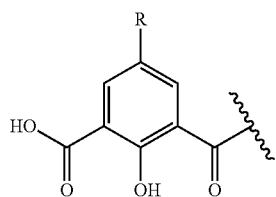

(I)

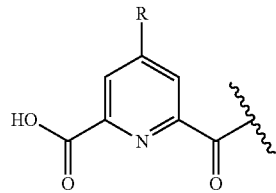

-continued (II)

11 Claims, 5 Drawing Sheets

(51) Int. Cl.
    *B82Y 5/00* (2011.01)
    *B82Y 20/00* (2011.01)
    *B82Y 30/00* (2011.01)
    *B82Y 40/00* (2011.01)

(52) U.S. Cl.
    CPC .............. *B82Y 20/00* (2013.01); *B82Y 30/00* (2013.01); *B82Y 40/00* (2013.01)

FIG.7
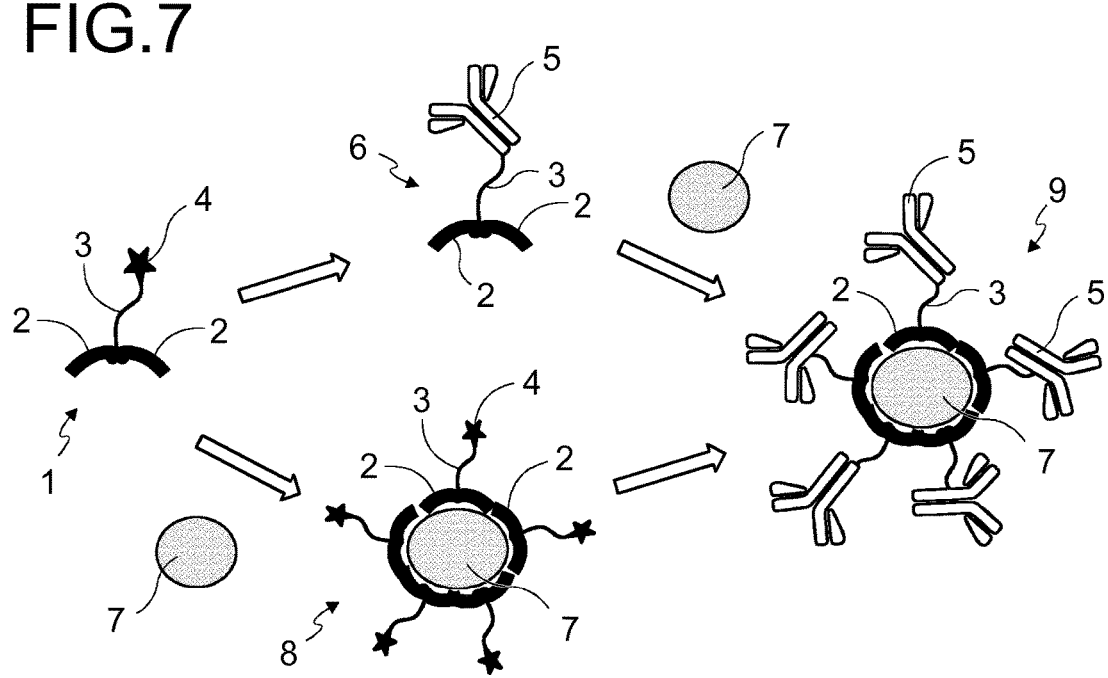
FIG.9
FIG.8
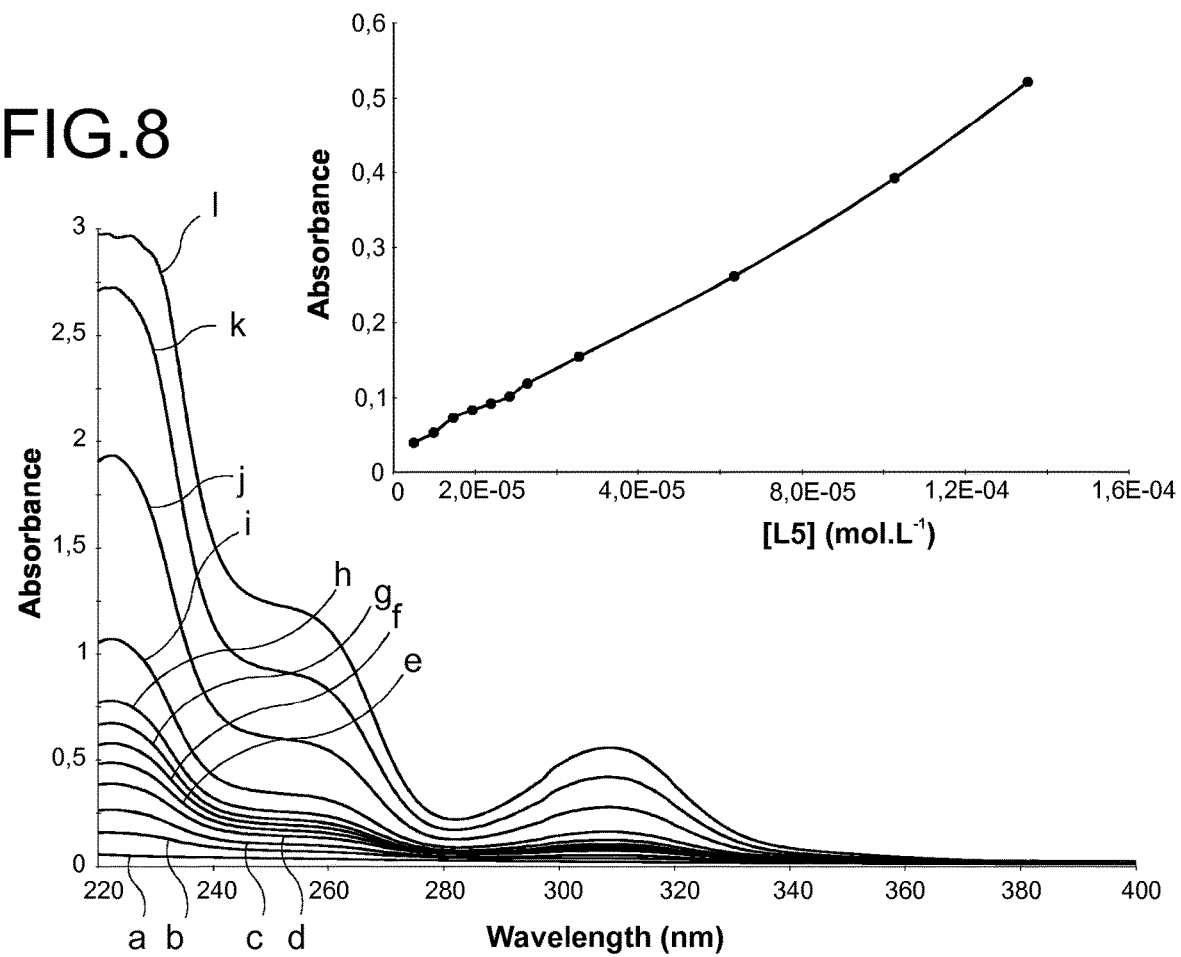

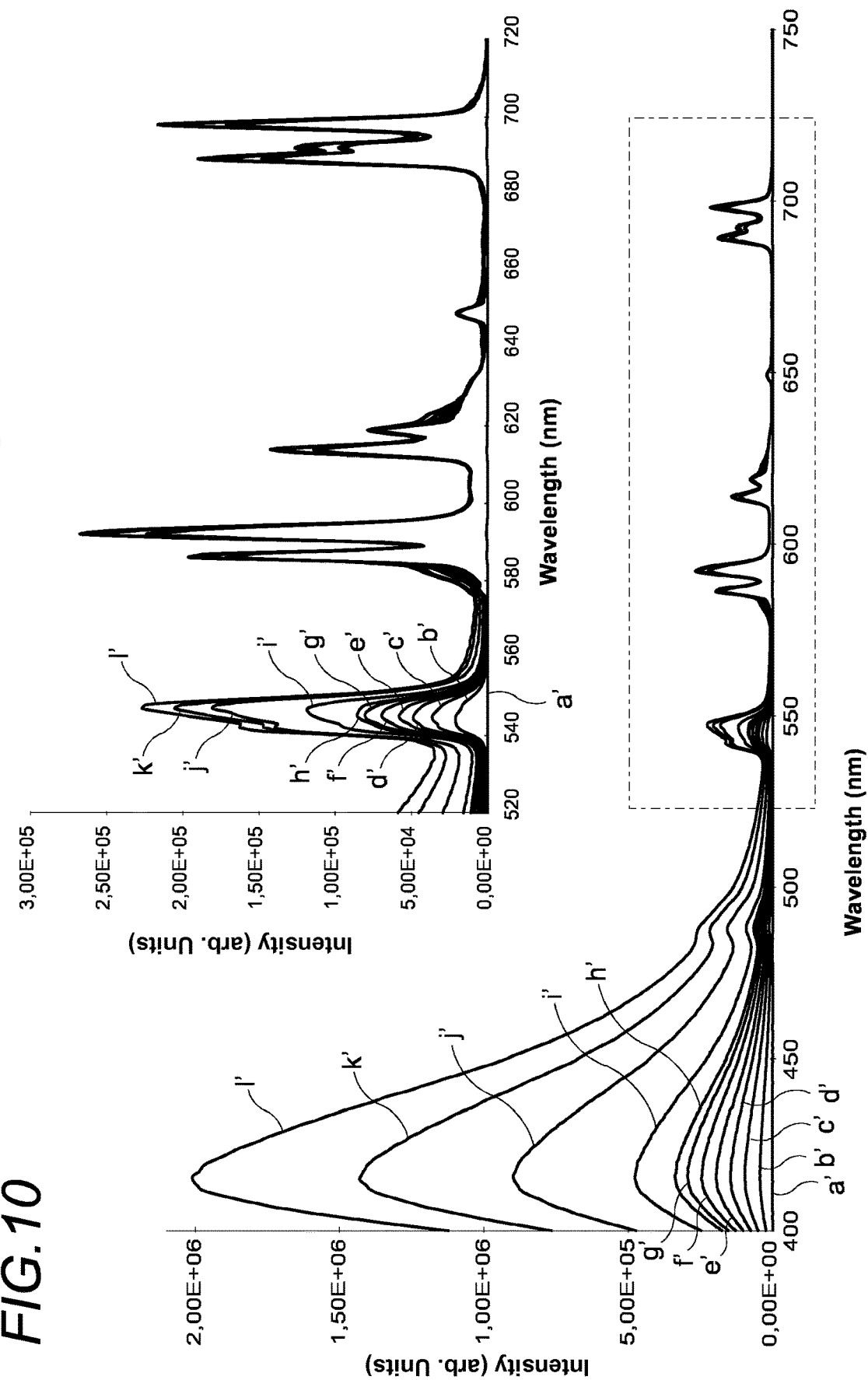

ULTRABRIGHT LUMINESCENT LANTHANIDE NANOPARTICLES COMPRISING TERBIUM, WITH LONGER EXCITED-STATE LIFETIME

TECHNICAL FIELD

The present invention relates to new luminescent lanthanide nanoparticles with important brightness and very long lifetime of the excited-state.

More particularly, it concerns terbium ion nanoparticles co-doped with ions of a second lanthanide, including chromophore ligands that coats the surface thereof, that result in both an improved brightness and an increased lifetime of the excited-state.

These luminescent nanoparticles can advantageously be used in the technical fields of biological analysis, particularly for fluoro-immunological analysis, medical imaging and microscopy.

BACKGROUND OF THE INVENTION

In biological analysis field, there is important need for "label" compounds which are able to specifically bind to a bio-molecule and are easily observable.

Thanks to these label compounds, the presence of particular analytes, such as for example nucleic acids, enzymes, peptides, pharmaceuticals (e.g. narcotics, poisons, drugs . . . ), hormones, metabolites, pathogenic microorganisms, viruses or antibodies, and especially those implicated in disease states, can advantageously be detected and quantified, for research or diagnostic purpose.

Preferred labels should be inexpensive, safe, stable and capable of being attached to a wide variety of chemical, biochemical and biological materials. They should be rarely, and rather never, found in nature. Further, they should give a highly characteristic signal, easily detectable in aqueous systems, preferably in a rapid, sensitive and reproducible way.

A wide variety of labels have been developed in prior art. For example, radioactive labels are sometimes used. But such labels have disadvantages, because they are expensive, hazardous, require sophisticated equipment and trained staff, and need specific waste treatment.

In that context, labels that are directly detectable using fluorescence spectroscopy or luminescence detection methods are of particular interest. A large number of such labels, developed for their facile attachment to other molecules, have been described in prior art and some are commercially available. Such labels should ideally possess a good brightness, defined as the product of the molar extinction coefficient by the luminescence quantum yield, narrow emission bands and long excited state lifetime, allowing for time-resolved detection techniques.

Semi-conducting nanocrystals, also called quantum dots, for example those described by Medintz et al, *Nature Materials*, June 2005, 4, 435 possess good brightness but have very short luminescence lifetimes (less than the microsecond) and broad emission peaks.

Lanthanides ions possess very particular spectroscopic properties and are interesting candidates to be used in such luminescent labels, as disclosed by Bünzli, J. C. G. *Chem. Rev.* 2010, 110, 2729. Indeed, their emission lines are very narrow and their excited-states lifetimes are long and can reach few milliseconds. Discrimination, both spectral and temporal, of their luminescence signal is thus possible with a reasonable signal-to-noise ratio.

However, the corresponding molar extinction coefficients are very small, thus generating a very low brightness. To overcome this inconvenience, photo-sensitizing ligands have been used to absorb light and transfer absorbed energy towards the lanthanide ions, thanks to a mechanism called antenna effect.

Luminescent labels based on lanthanide ion mononuclear complexes capable of binding to biological material exist in prior art and some are commercially available (under Lumi4 or Lanthascreen commercial names for example). Patent applications WO 00/48990 and WO 00/48991 disclose examples of such luminescent markers made from a lanthanide ion chelate comprising one lanthanide ion and a complexing agent.

However, the best known lanthanide based labels still display modest brightness, because of the molecular nature of these complexes. The most efficient molecular complexes, for example described in WO 2013/011236; Delbianco, M. et al, *Angew. Chem. Int. Ed.* 2014, 54, 10718; WO 2006/001835 or Xu, J. et al, *J. Am. Chem. Soc.* 2011, 133, 199900, have a brightness in the order of $10^4$ $M^{-1}\cdot cm^{-1}$ and modest luminescence lifetimes never exceeding 3 ms.

To improve this aspect, the present inventors were interested in lanthanide ion nanoparticles instead of lanthanide ion molecular complexes.

Nanoparticles are small objects, which are sized between 1 nm and 500 nm according to an usual definition, and are composed of numerous atoms, one interest of which is due to the high number of atoms at the surface. With recent innovations in the field, the synthesis of nanoparticles can be controlled in terms of size, elemental composition and properties.

Lanthanide nanoparticles are very promising as biological markers since they offer large Stoke's shifts and strong photostability. But, even if they are constituted of several hundreds or thousands lanthanide cations, lanthanide ion nanoparticles also have low absorption coefficients.

However, the inventors have studied the photo-sensitization of lanthanide ion nanoparticles, particularly of terbium containing lanthanide ion nanoparticles and have succeeded in raising the brightness thereof upper than $10^6$ $M^{-1}\cdot cm^{-1}$, i.e. two orders of magnitude above the brightness of efficient molecular complexes, by coating them with suitable chromophore ligands performing antenna effect with surface terbium ions. They have thus obtained new ultrabright luminescent terbium nanoparticles that can be marked by vectors (carrier molecules) of analytical interest to be used as labels.

Further, to improve the sensitivity in analyses compared to those realized with lanthanide ion mononuclear complexes described in prior art, it is highly desirable to extend the excited-state lifetime of the markers.

Indeed, with a longer excited-state lifetime, it is possible to realize time-resolved measurements with a delayed signal acquisition. After a pulsed excitation, a delay before recording the emitted intensity is imposed. This delayed acquisition removes the shorter fluorescent phenomena and the signal of all other fluorescent molecules disappears. Only, the phosphorescent signal of longest excited-state lifetime compounds is still present to be measured. The background noise is thus significantly decreased, and the signal-to-noise ratio substantially increased. This is a considerable advantage in biological media where fluorescent compounds are numerous in the environment.

The new luminescent nanoparticles containing terbium provided by the invention, in addition to an important brightness and an ability to bind vectors of analytical interest allowing an utilisation as labels, further have a longer excited-state lifetime than prior art compounds.

By improving the sensitivity and the signal resolution of measurements, these very long excited-state lifetime and exceptional brightness in aqueous solution of the nanoparticles of the invention enable exceptional results in biological analyses and microscopy fields.

DESCRIPTION OF THE INVENTION

To solve the technical problem, the invention provides a luminescent lanthanide nanoparticle, having at the same time an improved brightness and an increased lifetime of the excited-state, and comprising a lanthanide ion nanoparticle including terbium, and several molecules of chromophore ligand that are bonded to the surface of the lanthanide ion nanoparticle.

According to the invention, said lanthanide ion nanoparticle comprises terbium ions and ions of at least a second lanthanide selected from the group consisting of: cerium, praseodymium, neodymium, samarium, europium, dysprosium, holmium, erbium, thulium and ytterbium.

Further, said ligand is an organic molecule comprising at least one chromophore radical of formula I or of formula II:

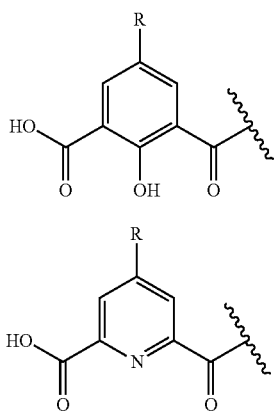

wherein R is selected from H, CN group or COOH group.

According to an embodiment of the invention, said lanthanide ion nanoparticle comprises terbium ions and ions of at least a second lanthanide selected from the group consisting of: cerium, praseodymium, neodymium, samarium, europium, dysprosium, holmium, erbium, thulium and ytterbium.

Further, said ligand is an organic molecule comprising at least one chromophore radical of formula I or of formula II:

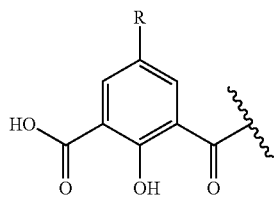

-continued

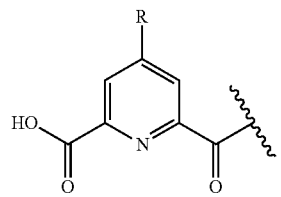

wherein R is 4-ethylbenzoic acid group.

The ligand is thus an organic molecule including one group or motif with the formula I or II as described above, and any suitable chemical structure linked to said group or motif. This chemical structure of any kind, situated after the represented truncation, may be for example a OH group, a branched, linear or cyclic carbon chain with or without heteroatoms, a grafting function, one or several other chromophore group(s) optionally linked together by a spacer group of any suitable kind, or any other suitable chemical structure.

Thanks to the invention, the obtained nanoparticles have a brightness and an excited-state lifetime that are simultaneously superior to 3 ms and $10^4$ $M^{-1} \cdot cm^{-1}$ respectively, preferentially simultaneously superior to 5 ms and $10^5$ $M^{-1} \cdot cm^{-1}$ respectively, and even more preferentially simultaneously superior to 7 ms and $10^6$ $M^{-1} \cdot cm^{-1}$ respectively, when measured as described in the Example part thereafter, in the section called: "Experimental measurement methods of luminescence spectroscopy".

According to an embodiment of the invention, the second lanthanide is selected from europium, samarium, dysprosium and ytterbium, and is preferentially europium.

Depending on the embodiments, the lanthanide ion nanoparticle may contain between 10 and 99.9 mol. %, preferentially between 50 and 99.9 mol. %, and even more preferentially between 75 and 99.9 mol. % of terbium ions, and between 0.1 and 90 mol. %, preferentially between 0.1 and 50 mol. %, and even more preferentially between 0.1 and 25 mol. % of ions of the second lanthanide.

According to a preferred embodiment of the invention, the lanthanide ion nanoparticle further comprises ions of a third lanthanide selected from lanthanum, lutetium and gadolinium, and being preferentially lanthanum.

In this case and depending on the embodiments, said lanthanide ion nanoparticle may contain between 1 and 98.9 mol. %, preferentially between 10 and 98 mol. %, and even more preferentially between 40 and 98 mol. % of terbium ions, between 0.1 and 20 mol. %, preferentially between 0.5 and 10 mol. %, and even more preferentially between 1 and 5 mol. % of ions of the second lanthanide, and between 1 and 90.9 mol. %, preferentially between 10 and 80 mol. %, and even more preferentially between 10 and 20 mol. % of ions of the third lanthanide.

According to an embodiment of the invention, the ligand comprises n chromophore radicals and a spacer group, wherein the spacer group is a heteroatom containing carbon chain that links together the chromophore radicals and wherein n is an integer from 1 to 10, preferentially from 2 to 6 and more preferably from 2 to 3.

According to a preferred embodiment of the invention, the ligand further comprises a grafting function able to be covalently linked to a carrier molecule of analytical interest.

According to this embodiment, the luminescent nanoparticle may further comprise a carrier molecule of analytical interest covalently attached to at least one ligand molecule.

The carrier molecule of analytical interest is preferably selected from the group consisting of: peptides, proteins, antibodies, antibody moieties and small molecules of molecular weight lower than 2000 g·mol$^{-1}$. It can be, for example, biotin, desthiobiotin, streptavidin or Matuzumab antibody, peptide LPFFD, peptide KLVFF, or Anti-IgG (H+L) human antibody.

According to a preferred embodiment of the invention, the ligand is selected from molecules having a structure according to formula L1, L2, L3, L4 and L5:

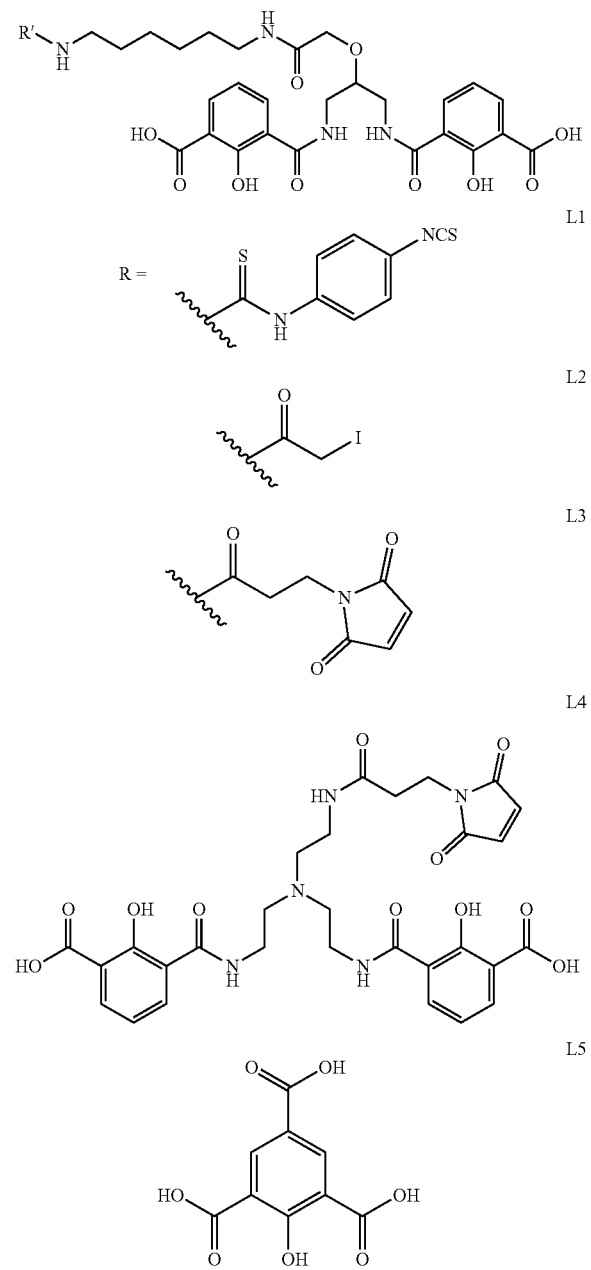

According to another preferred embodiment of the invention, the ligand is selected from molecules having a structure according to formula L6, L7, L8 and L9:

BRIEF DESCRIPTION OF THE FIGURES

Other characteristics and advantages of the invention will be revealed by reading the detailed description that follows, referring to the attached illustrations, in which:

FIG. 7 is a schematic representation of two different ways to obtain bio-functionalized luminescent nanoparticles according to the invention;

FIGS. 8 and 10 are graphs illustrating the titration of lanthanide nanoparticles according to example N°6 by ligand L5 followed, respectively, by UV/visible absorption and by emission fluorescence spectroscopy;

FIG. 9 is a graph relative to the titration of FIG. 8 that shows the absorption evolution at 314 nm as a function of the concentration of added ligand L5;

FIG. 11 is an enlargement of the surrounded portion of FIG. 10 graph showing more particularly the area of the spectrum corresponding to the emission of terbium and europium;

DETAILED DISCLOSURE OF THE INVENTION

Figure 1:
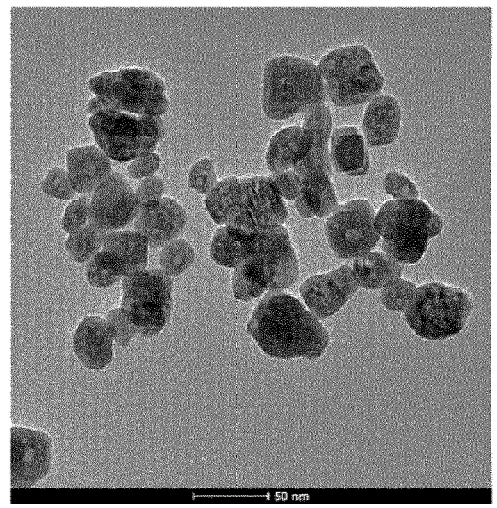
FIGS. 1 to 3 are, respectively, a transmission electron microscopy image, a graph illustrating dynamic light scattering in ultrapure water and a graph showing X-ray diffraction pattern of solid nanoparticles, corresponding to lanthanide nanoparticles according to example N°5.
Figure 2:
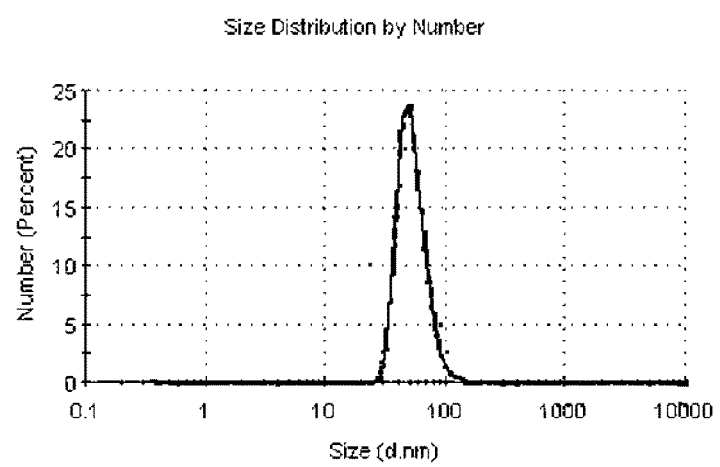
Figure 3:
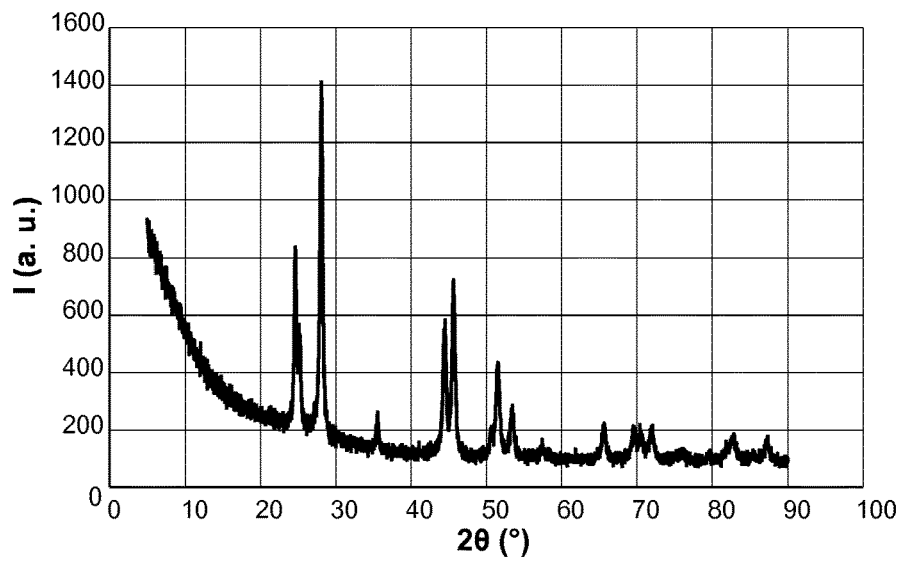
Figure 4:
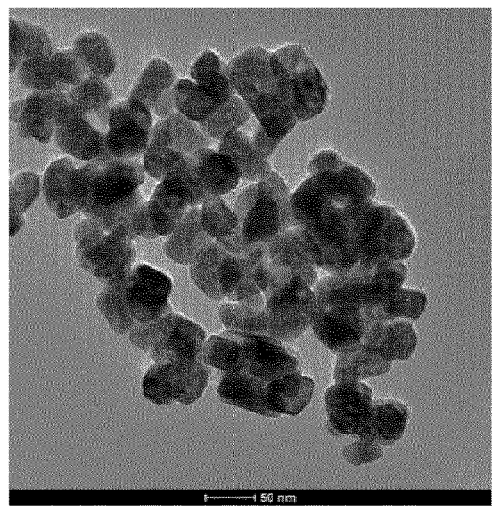
FIGS. 4 to 6 are respectively a transmission electron microscopy image, a graph illustrating dynamic light scattering in ultrapure water and a graph showing X ray diffraction pattern of solid particles, corresponding to lanthanide nanoparticles according to example N°6.
Figure 5:
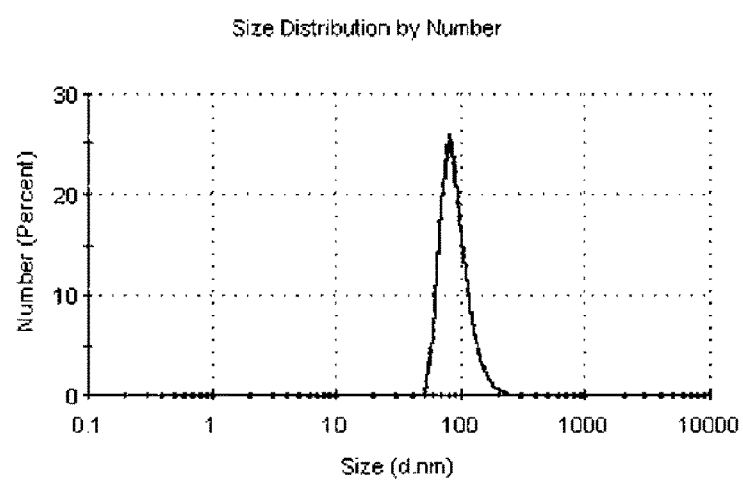
Figure 6:
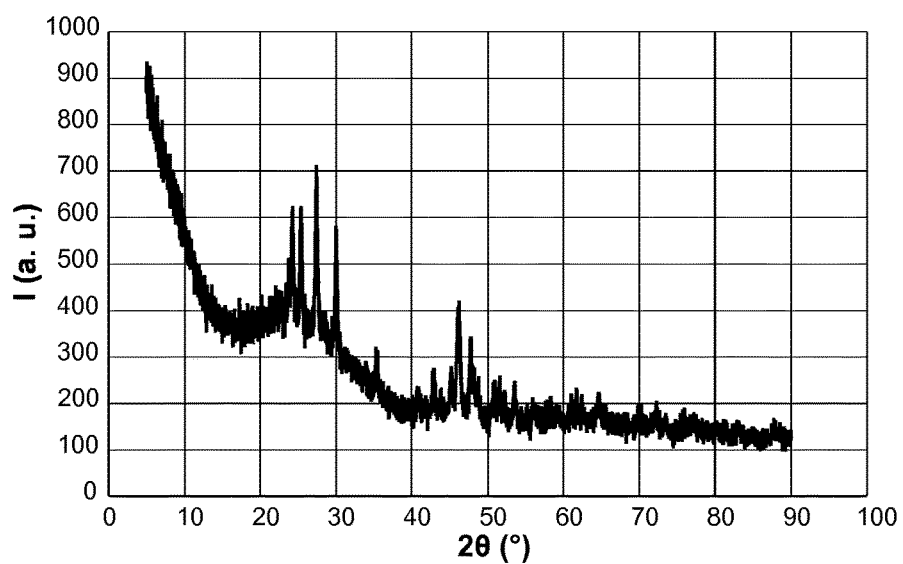

Luminescent nanoparticles according to the invention will now be described in detail with reference to the FIGS. 1 to 13.

Unless defined otherwise, all technical and scientific terms used herein have the meaning commonly understood by a person skilled in the art to which the invention belongs.

The luminescent nanoparticle according to the invention is made from a lanthanide ion nanoparticle comprising terbium ions and ions of at least a second lanthanide selected from cerium, praseodymium, neodymium, samarium, europium, dysprosium, holmium, erbium, thulium and ytterbium.

Preferably, this lanthanide ion nanoparticle may also contain ions of a third lanthanide, acting as a host matrix that is spectroscopically silent in the visible and near infrared regions, but that advantageously decreases the self-quenching between the spectroscopically active ions.

These third lanthanide ions can advantageously be lanthanum ions or lutetium ions that can easily be doped by terbium ions and ions of another lanthanide (second lanthanide ions) to obtain the co-doped lanthanide ion nanoparticle of the invention.

If magnetic properties are desired, besides spectroscopic properties, gadolinium ions can also advantageously be used as third lanthanide ions.

The lanthanide ion nanoparticles can be easily synthetized in water medium by a person skilled in the art using classical available methods. They can for example be realized in water using a microwave oven or by hydrothermal synthesis in an autoclave as is explained in details in the Example part thereafter.

When synthetized accordingly, the different lanthanide ions are randomly situated, some on the surface and some in the core of the obtained nanoparticle.

Many lanthanide ion nanoparticles in compliance with the invention were synthetized and characterized by the inventors with different doping levels in terbium and other lanthanides ions. Several examples thereof are gathered in Table 1 of Example part thereafter.

Lanthanide ion nanoparticles corresponding to example N°5 and N°6 were characterized by transmission electron microscopy, dynamic light scattering in ultrapure water and X-ray diffraction. The obtained results are illustrated in FIGS. 1 to 6.

As previously explained, the luminescent nanoparticles of the invention are photosensitized by chromophore ligands These chromophore ligands absorb light energy and transfer it to the lanthanide ions present at the surface of the nanoparticle by antenna effect.

The choice of the nature of these ligands is important to have an excellent coordination to ensure the solubility and stability of the nanoparticle, and to get desired remarkable spectroscopic properties.

The ligands according to the invention are chosen with one or several chromophore radicals that specifically photosensitize terbium ions, these chromophore radicals being able to transfer an energy amount corresponding at least to the energy gap of 7F6 to 5D4 transition of terbium.

For that reason, chromophore radicals based on dipicolinic acid or 2-hydroxyisophthalic acid fluorophores have been chosen to sensitize Tb(III) ions of the nanoparticle according to the invention. Indeed, the triplet state of these radicals (respectively 26600 $cm^{-1}$ and approximately 23000 $cm^{-1}$) is close to the excited state of Tb(III) ions (20500 $cm^{-1}$) and allow to optimize the energy transfer and to get an excellent photosensitization.

The formulas of dipicolinic acid (at left) and 2-hydroxyisophthalic acid (at right) are shown below:

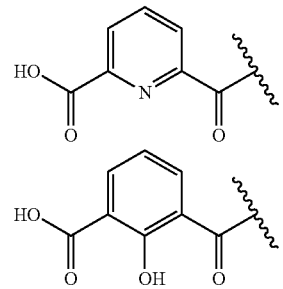

From these observations, two series of ligands have been synthesized with different linkers and substituents. However, in contradiction to usual ligands used for lanthanide ions coordination which are highly preorganized, the ligands of the invention preferentially target a planar coordination to ensure the stabilization of the nanoparticles while preventing leaching from the lanthanide cations.

Accordingly, the present invention provides advantageous ligands which comprise one or several chromophore radicals of formula I or of formula II:

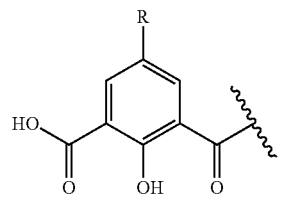

-continued

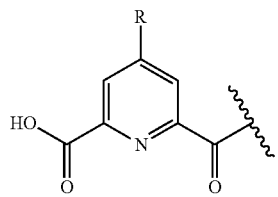

wherein R is selected from H, CN group or COOH group.

According to another embodiment, the present invention provides advantageous ligands which comprise one or several chromophore radicals of formula I or of formula II:

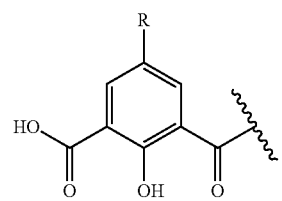

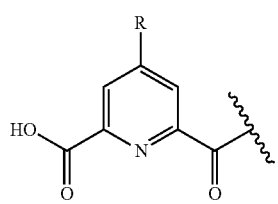

wherein R is 4-ethylbenzoic acid group.

These chromophore radicals have several oxygen and nitrogen atoms serving as anchorage points that ensure the attachment of the ligand to the surface of the lanthanide nanoparticle, and an aromatic part able to strongly absorb light energy and to subsequently transfer it to terbium ions at the surface of the lanthanide nanoparticle where it is attached.

An example of ligand in compliance with the invention is in particular the below-represented molecule called L5:

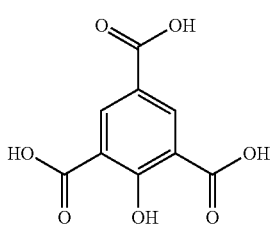

Four other preferential examples of ligands, called L1, L2, L3 and L4, are shown thereafter:

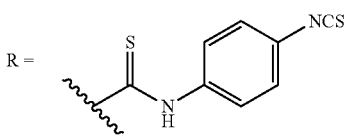

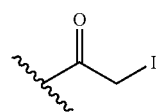

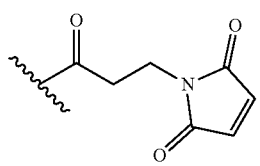

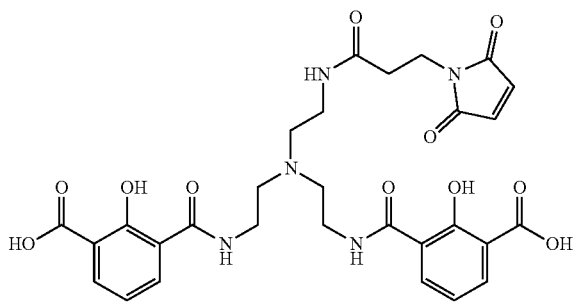

Four other preferential examples of ligand, called L6, L7, L8 and L9, are shown thereafter:
The synthesis methods of those ligand examples L1 to L5 are described in the below Example part.
L6
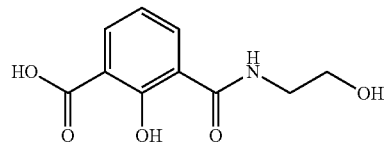
L7
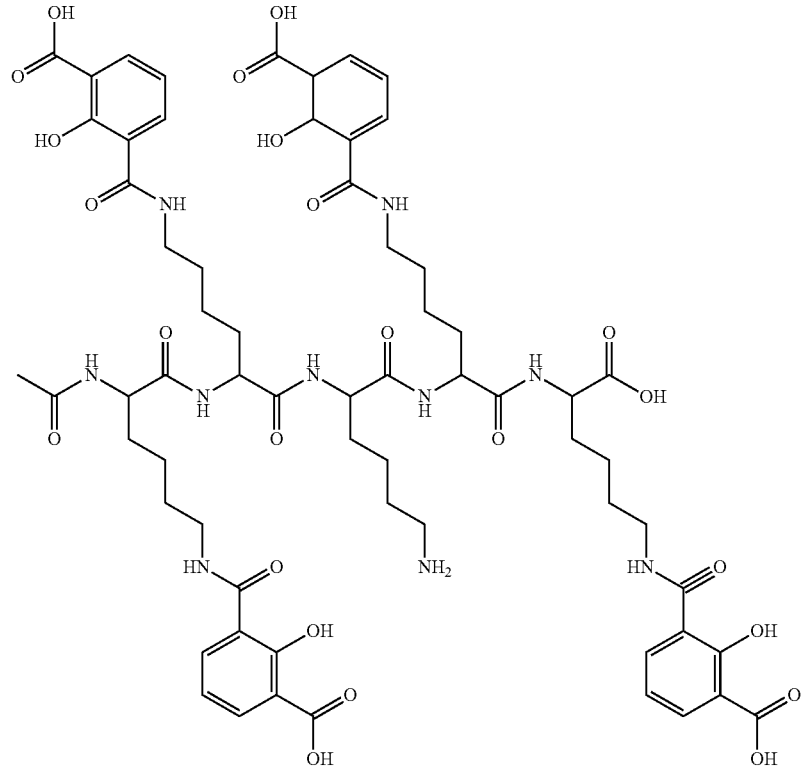
L8
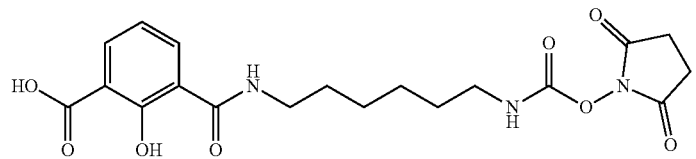
L9
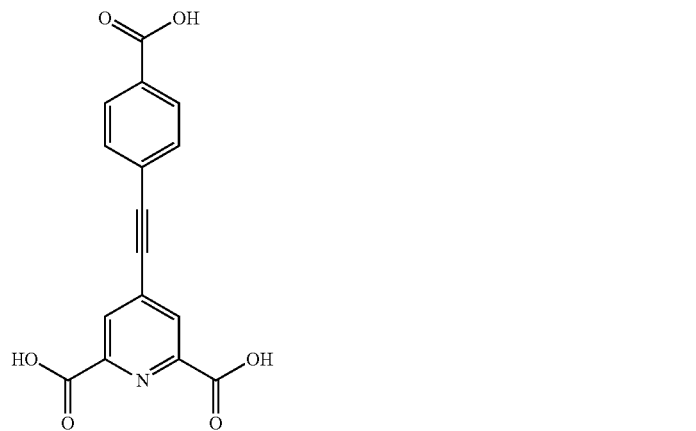

The synthesis methods of those ligand examples L6 to L9 are also described in the below Example part.

When the ligand comprises several chromophore radicals, these radicals are preferentially linked together within the ligand, by a carbon chain, called spacer group, having a length increasing with the number of chromophore radicals of the ligand.

As can be seen with L1 to L4, the spacer group is preferentially a branched carbon chain containing one or several heteroatoms, for example nitrogen atoms, with at least as many arms as chromophore radicals to link.

Furthermore, we can see the same with L6 to L8, the spacer group is preferentially a branched carbon chain containing one or several heteroatoms, for example nitrogen atoms, with at least as many arms as chromophore radicals to link.

Advantageously, the ligand according to the invention may further comprise a grafting function able to covalently attach a carrier molecule of analytical interest. In this case, this grafting function is also linked to the rest of the molecule by the spacer group.

In the case of the above-described embodiment, the spacer group may have a supplemental arm to link the grafting function.

The nature of the grafting function is determined in function of the nature of the vector or carrier molecule to attach. Its chemical structure is elaborated to be able to specifically and covalently link to the chemical structure of the desired carrier molecule. This grafting structure can thus be adapted by a person skilled in the art to correspond exactly to the desired application.

The aimed carrier molecules can be diverse, depending on the wished label or marker to obtain. Several of such vectors have been envisaged and are compatible with the invention, including for example peptides, proteins, antibodies, antibody moieties, or small molecules of molecular weight lower than 2000 g·mol−1 such as biotin or desthiobiotin for example.

In another embodiment, others vectors have been envisaged and are compatible with the invention, including for example peptide LPFFD, peptide KLVFF, or Anti-IgG (H+L) human antibody.

After fixation of the ligands around the lanthanide ion nanoparticle and covalent attachment of a carrier molecule of analytical interest to the ligands, bio-functionalized ultrabright luminescent nanoparticles are obtained thanks to the invention.

As schematically represented on FIG. 7, two different ways are possible to obtain such bio-functionalized luminescent nanoparticles, depending on the order in which the steps are realized.

According to the first way, represented above, ligand molecules 1, each comprising a chromophore radical 2, a spacer group 3 and a grafting function 4, are first mixed with biomolecules 5 (carrier molecules or vectors), that can be for example peptides or antibodies. These biomolecules 5 bind to ligand molecules 1 via their grafting function 4 and bio-functionalized ligand molecules 6 are obtained.

In a second step, lanthanide nanoparticles 7 are mixed to the bio-functionalized ligand molecules 6 which coat the surface of the lanthanide nanoparticles 7 by means of their chromophore radicals 2.

According to the second way, represented below, ligand molecules 1 are immediately brought into contact with lanthanide nanoparticles 7. The chromophore radicals 2 of the ligand molecules 1 bind to the surface of lanthanide nanoparticles 7 thus forming coated nanoparticles 8.

These coated nanoparticles 8 are mixed with biomolecules 5 in a second step. These biomolecules 5 covalently bind to the grafting function 4 of ligand molecules 1 already attached to the lanthanide nanoparticles 7.

Both described ways result in the obtention of biofunctionalized luminescent nanoparticles 9 according to the invention. Because of steric hindrance due to biomolecules 5, they differ in the number of fixed coating ligands (more important in the second way) and in the number of fixed biomolecules (more important in the first way) and can thus be alternatively chosen by a person skilled in the art depending on the targeted application.

Accordingly, the previously described ligands L1 to L4 can advantageously fix carrier molecules of analytical interest, by means of reaction of the hydroxyl, amine or thiol functions of the carrier molecules, for example, with the grafting functions of ligands L1 to L4, in order to produce bio-functionalized ligands.

Two particular examples of bio-functionalized ligands realized from ligand L1 have been synthesized and tested by the present inventors. These examples, relative to biofunctionalization of ligand L1 by streptavidin and by Matuzumab antibody, are described in detail in the Example part thereafter.

Further to advantageously bio-functionalize luminescent nanoparticles, the invention provides luminescent nanoparticles with exceptional spectroscopic properties.

As previously explained, the coating of the lanthanide ion nanoparticles by suitable chromophore containing ligands improve the brightness of the resulting nanoparticles thanks to energy transfer via antenna effect from chromophores to the terbium ions situated at the surface of the nanoparticle.

However, those surface terbium ion are subject to vibrational quenching by water molecules of the aqueous environment surrounding them in biological medium, that disadvantageously reduces their excited-state lifetime and decreases their quantum yield, and thus subsequently their brightness.

To solve this technical problem the invention provides lanthanide nanoparticles that comprise, in addition to terbium ions, ions of a suitable second lanthanide different from terbium.

The goal of this addition of second lanthanide ions is to promote the luminescence of the lanthanide ions situated in the core of the nanoparticle.

Indeed, lanthanide ions situated in the core of the nanoparticle have longer lifetimes and improved intrinsic quantum yields than surface ions since they are protected from vibrational quenching of water molecules of the medium. But, they are nevertheless far from the surface and cannot be sensitized efficiently by the chromophore ligands acting as an antenna.

By introducing ions of a second lanthanide, appropriately selected among cerium, praseodymium, neodymium, samarium, europium, dysprosium, holmium, erbium, thulium and ytterbium to be able to cooperate with terbium ions, the luminescent participation of these core ions is advantageously obtained.

Indeed, an energy transfer from terbium ions $Tb^{3+}$ situated at the surface of the nanoparticles to ions of the second lanthanide $Ln^{3+}$ which are present in the core of the nanoparticles is promoted by funnel effect.

Thanks to this efficient energy transfer, surface terbium ions act as a relay to access and photosensitize core lanthanide ions. Accordingly, the spectroscopic properties of the nanoparticles are enhanced. The brightness of the nanoparticles is improved and their excited-state lifetime in aqueous medium is increased simultaneously.

Such advantageous effects have been demonstrated in FIGS. 8 to 13 relating to studies carried out on luminescent nanoparticles in compliance with the invention and comprising lanthanide nanoparticles according to example N°6 coated with ligand L5 molecules.

These studies have been carried out to understand the behaviour of example N°6 lanthanide nanoparticles in presence of ligand L5. Through titrations by L5, the absorption, excitation and emission spectra of the nanoparticles have been monitored. The objective of these tests was to show that the sensitization of Tb(III) ions by L5 improves the spectroscopic properties in water of Eu(III) ions of the nanoparticle using the energy transfer between Tb and Eu.

In FIG. 8, a buffer solution (TRIS/HCl, 0.01 M, pH=7) containing La0.14Tb0.85Eu0.01F3 nanoparticles ([c]=13.5 pM) has been titrated by the ligand L5. That operation has consisted to add increasing volumes of an aqueous solution of L5 ([c]=$5 \times 10^{-4}$ M) and to monitor the absorption of the resulting solution by UV/visible absorption spectroscopy.

Each curve, a to 1, correspond to a different increasing added volume V of ligand L5 solution.

Curve a corresponds to the nanoparticle solution alone, without ligands L5, that is to an added volume of $V_a$=0 µL of L5 ligand solution.

Curves b to 1 correspond respectively to an added volume of L5 ligand solution of $V_b$=20 µL for curve b, $V_c$=40 µL for curve c, $V_d$=60 µL for curve d, $V_e$=80 µL for curve e, $V_f$=100 µL for curve f, $V_g$=120 µL for curve g, $V_h$=140 µL for curve h, $V_i$=200 µL for curve i, $V_j$=400 µL for curve j, $V_k$=650 µL for curve k and $V_l$=900 µL for curve 1.

As can be observed on FIG. 8, the absorption of the solution increases in the same way as the volume of added ligand.

If the absorption at 314 nm, corresponding to the maximum of the absorption band of the ligand L5, is specifically studied as represented on FIG. 9, it can be noticed that the increase of the absorption band at 314 nm is linear as a function of the concentration of added ligand.

At the same time, the emission spectra of $La_{0.14}Tb_{0.85}Eu_{0.01}F_3$ nanoparticles were also measured by fluorescence spectroscopy (with $\lambda_{exc}$=330 nm) for each addition of L5 and represented on FIGS. 10 and 11, each curve a' to 1' corresponding to a different increasing added volume of ligand L5 solution.

As previously, curve a' corresponds to the nanoparticle solution alone, without ligands L5, that is to an added volume of $V_a'$=0 µL of L5 ligand solution, and curves b' to 1' correspond respectively to an added volume of L5 ligand solution of $V_b'$=20 µL for curve b', $V_c'$=40 µL for curve c', $V_d'$=60 µL for curve d', $V_e'$=80 µL for curve e', $V_f'$=100 µL for curve f', $V_g'$=120 µL for curve g', $V_h'$=140 µL for curve h', $Y_i'$=200 µL for curve i', $V_j'$=400 µL for curve j', $V_k'$=650 µL for curve k' and $V_l'$=900 µL for curve 1'.

The chosen excitation wavelength, $\lambda$exc=330 nm, corresponds to an absorption wavelength of ligand L5.

Curve a' corresponding to the nanoparticles solution without ligands L5 shows that when excited at 330 nm, the Tb and Eu emissions of the nanoparticles are extremely weak. Curve a' nearly coincides with the abscissa axis.

The first addition of ligand corresponding to curve b' allows to sensitize Tb and Eu ions to obtain an emission spectrum containing the four typical emission bands of terbium at 485, 545, 584 and 621 nm and the signal of europium with narrow bands at 579 nm, 583-603 nm, 604-630 nm, 650 nm and 679-707 nm with the maximum of emission at 592 nm.

The importance of these emission bands increase in the same ways as the added quantity of ligands increases, from curve b' to curve 1').

The emission bands corresponding to terbium and europium can be more easily observed on the enlargement of FIG. 11.

Another emission band in the area of 415 nm appears and increases when large amounts of ligand are added. This band is due to the fluorescence of the ligand in solution.

Figure 12:
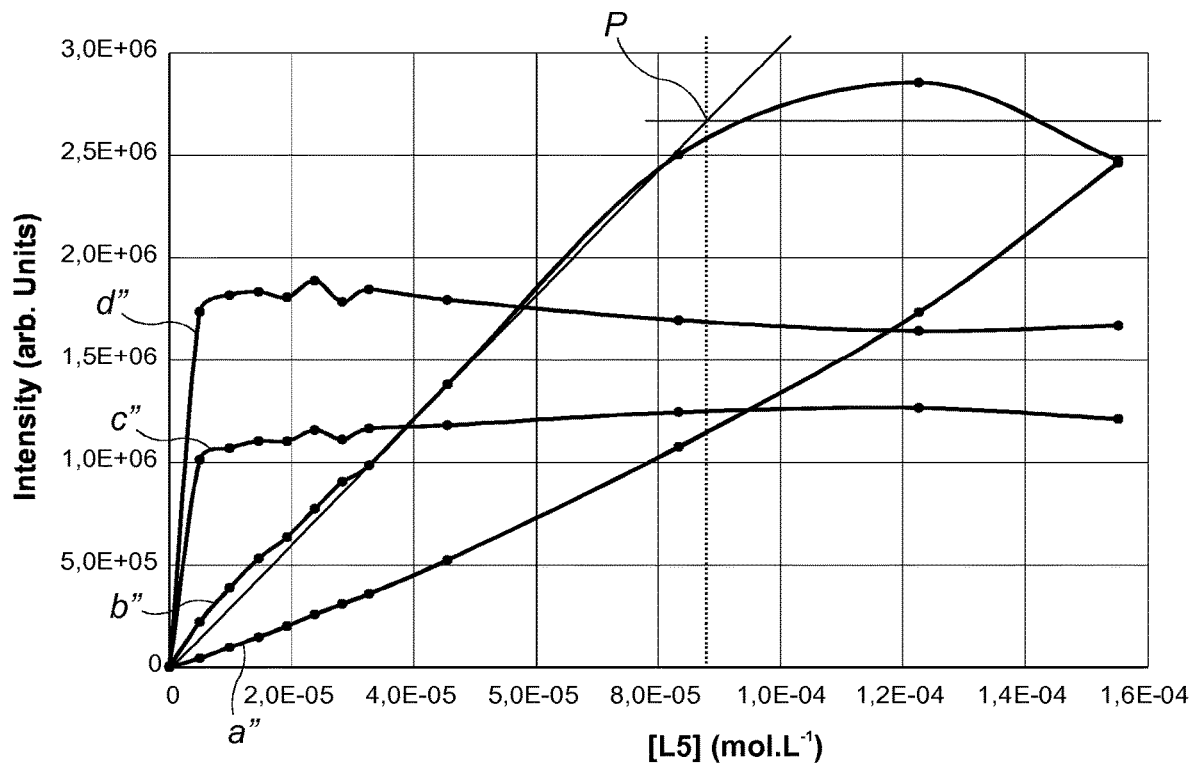
FIG. 12 is a graph relative to the titration of FIG. 10 that shows the intensity emission evolution at different wavelengths as a function of the concentration of added ligand L5.

As can be observed on FIG. 12, evolution of the intensity of different peaks of the spectrum as a function of added ligand presents different behaviors during the titration with ligand L5.

Curve a" shows the evolution of the emission intensity at 415 nm, which corresponds to the emission band of ligand L5. As expected, curve a" is almost linear as a function of the concentration of added ligands. The slope of curve a" increases slightly after the equivalent volume (as explained below) because of the proliferation of uncoordinated ligand L5 molecules in the solution.

Curve b" shows the evolution of emission intensity for the main band of terbium at 545 nm. The emission intensity of terbium increases gradually in the first part of curve b", as the number of ligand L5 molecules bonded at the surface of the lanthanide nanoparticles increases. Then, a maximum is reached when the surface of the lanthanide nanoparticles is totally coated by ligand L5 molecules. This strong intensity emission is due to the photosensitization of terbium ions at the surface of the nanoparticles by the ligand L5 molecules.

The intersection at point P of the two straight lines related to the growing region and to the maximum region, allows defining the equivalent volume of the titration that corresponds to the minimal volume of ligand solution necessary to completely coat the nanoparticle surface. In the represented case, the equivalent volume was situated at 423 µL (corresponding to a concentration of $8.8 \times 10^{-5}$ mol. $L^{-1}$).

The evolution of europium emission has been observed on two bands at 614 nm and 700 nm corresponding respectively to curves c" and d". From the first addition of ligand L5 solution, a strong emission appears and reaches a maximum intensity for the two bands. This emission remains constant with the next additions of L5 solution.

Strong emission of europium ions shown by curves c" and d" proves that the photosensitization of terbium ions at the surface by the ligand L5 is advantageously followed by a quantitative transfer of the energy to europium ions within the core of the nanoparticles, as expected in the invention. This important emission cannot be caused by a direct photosensitization of europium ions present at the surface by the ligand L5, because ligand L5 molecules hardly photosensitize them as illustrated in FIG. 13.

Figure 13:
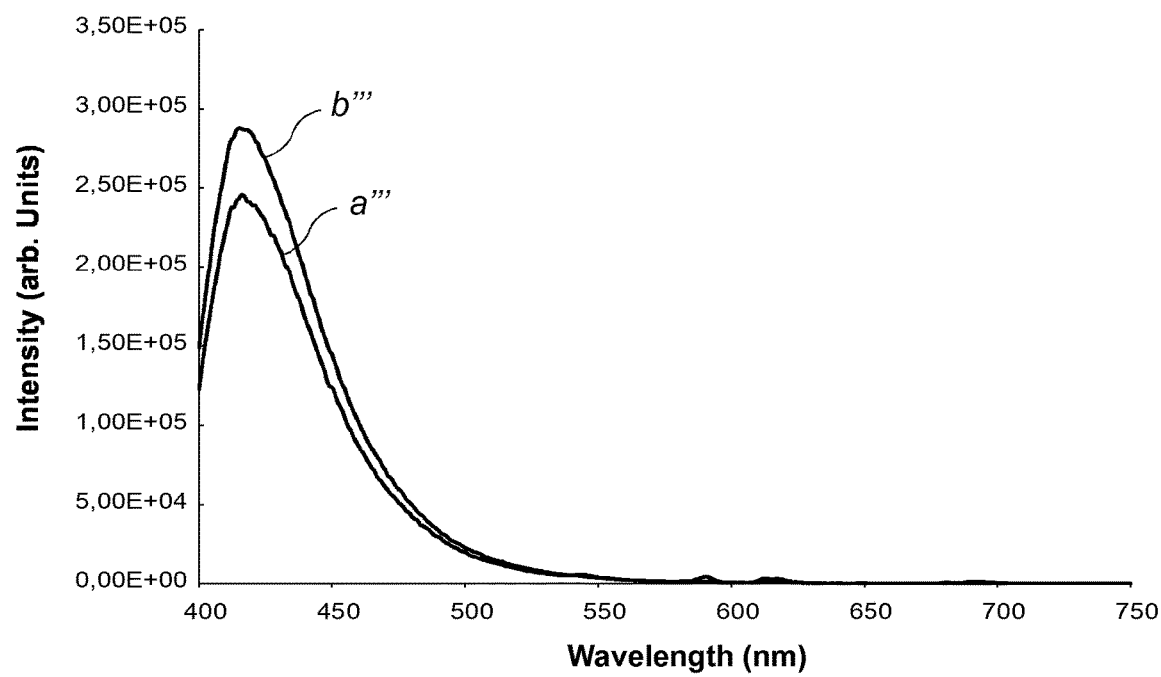
FIG. 13 is a graph showing the emission spectra of nanoparticles of $La_{0.99}Eu_{0.01}F_3$ (curve b''') and of $La_{0.9}Eu_{0.1}F_3$ (curve a''') coated with ligand L5 in a buffer solution.

Indeed, in FIG. 13, the emission spectra of two lanthanide nanoparticles containing europium ions but no terbium ions, respectively $La_{0.9}Eu_{0.1}F_3$ with a concentration of 1.29 nM for curve a''' and $La_{0.99}Eu_{0.01}F_3$ with a concentration of 246 pM for curve b''', have been monitored in presence of ligand L5 solution ([L5]=$1.22 \times 10^{-5}$ M) in a buffer solution (TRIS/HCl 0.01 M, pH 7.0) after an excitation at a wavelength of $\lambda$exc=330 nm corresponding to the ligand L5 absorption. On these spectra, the emission band of ligand L5 molecules is the only important emission peak visible, and almost no emission band of europium is observable.

EXAMPLE

Synthesis of the Lanthanide Ion Nanoparticles

Two experimental methods have been used for the synthesis of the lanthanide ion nanoparticles.

The first method uses microwave irradiation. It has been realized in water using a microwave oven.

According to this first method, solutions of $NH_4F$, $TbCl_3$, $LnCl_3$ and optionally $LaCl_3$ have been prepared in milliQ water. Ln correspond the second lanthanide of the nanoparticle of the invention and is alternatively cerium, praseodymium, neodymium, samarium, europium, dysprosium, holmium, erbium, thulium or ytterbium.

The first step of the synthesis has consisted in mixing together $TbCl_3$, $LnCl_3$ and optionally $LaCl_3$, in amounts corresponding to the desired co-doping for the nanoparticles.

In a second step, the solution of $NH_4F$ has been added at room temperature. This added volume of $NH_4F$ corresponded to three equivalents for 1 equivalent of lanthanides.

The third step was then to warm the mixture at 150° C. in a microwave oven for 12 min. The synthesis in microwave oven allowed to get a regular heating with a quick and precise temperature rise, quick synthesis at medium temperature and was therefore expected to produce nanoparticles with narrow size distribution.

After centrifugation during 25 minutes at 9000 tr/min, the supernatant was eliminated and the white solid was dispersed in milliQ water using ultrasounds for 1 h at 60° C. to obtain an aqueous suspension of the nanoparticles.

The second method is a hydrothermal synthesis in autoclave at 150° C. in water.

Except for the third step corresponding to the heating, the procedure was exactly the same. In the third step of this method, the mixture has been encapsulated in a steal reactor and has been heated in oven for 2 h at 150° C.

After centrifugation, supernatant elimination and ultrasound dispersion, an aqueous solution of the nanoparticles was obtained with a yield similar compared to the first method.

Different examples of lanthanide ion nanoparticles have been synthetized accordingly and are shown in table 1 below:

TABLE 1

| Example Number | Composition | Synthesis method | Yield (in %) | Volume (in mL) | Concentration (in mol. $L^{-1}$) |
|---|---|---|---|---|---|
| 1 | $La_{0.9}Tb_{0.05}Eu_{0.05}F_3$ | Hydrothermal | 29 | 25 | $1.72 \times 10^{-7}$ |
| 2 | $La_{0.9}Yb_{0.09}Tb_{0.01}F_3$ | Hydrothermal | 33 | 25 | $2.08 \times 10^{-7}$ |
| 3 | $La_{0.93}Tb_{0.06}Eu_{0.01}F_3$ | Hydrothermal | 37 | 25 | $1.56 \times 10^{-8}$ |
| 4 | $La_{0.76}Tb_{0.23}Eu_{0.01}F_3$ | Hydrothermal | 34 | 25 | $9.15 \times 10^{-8}$ |
| 5 | $La_{0.59}Tb_{0.40}Eu_{0.01}F_3$ | Hydrothermal | 29 | 25 | $1.11 \times 10^{-7}$ |
| 6 | $La_{0.14}Tb_{0.85}Eu_{0.01}F_3$ | Hydrothermal | 34 | 25 | $1.8 \times 10^{-9}$ |
| 7 | $Tb_{0.99}Eu_{0.01}F_3$ | Hydrothermal | 28 | 25 | $8.65 \times 10^{-11}$ |
| 8 | $La_{0.1}Tb_{0.85}Eu_{0.05}F_3$ | Microwave | 30 | 30 | |
| 9 | $La_{0.125}Tb_{0.85}Eu_{0.025}F_3$ | Microwave | 33 | 30 | |
| 10 | $La_{0.14}Tb_{0.85}Eu_{0.01}F_3$ | Microwave | 37 | 30 | |
| 11 | $La_{0.145}Tb_{0.85}Eu_{0.005}F_3$ | Microwave | 28 | 30 | |
| 12 | $La_{0.1475}Tb_{0.85}Eu_{0.0025}F_3$ | Microwave | 32 | 30 | |
| 13 | $La_{0.14}Tb_{0.85}Nd_{0.01}F_3$ | Microwave | 32 | 30 | |
| 14 | $La_{0.14}Tb_{0.85}Er_{0.01}F_3$ | Microwave | 30 | 30 | |
| 15 | $La_{0.14}Tb_{0.85}Tm_{0.01}F_3$ | Microwave | 29 | 30 | |
| 16 | $La_{0.14}Tb_{0.85}Dy_{0.01}F_3$ | Microwave | 33 | 30 | |
| 17 | $La_{0.14}TB_{0.85}Sm_{0.01}F_3$ | Microwave | 29 | 30 | |

Synthesis of the Ligands L1, L2 and L3

The claimed ligands L1, L2 and L3 were prepared by following the below synthesis steps and with the below intermediary compounds 1 to 7:

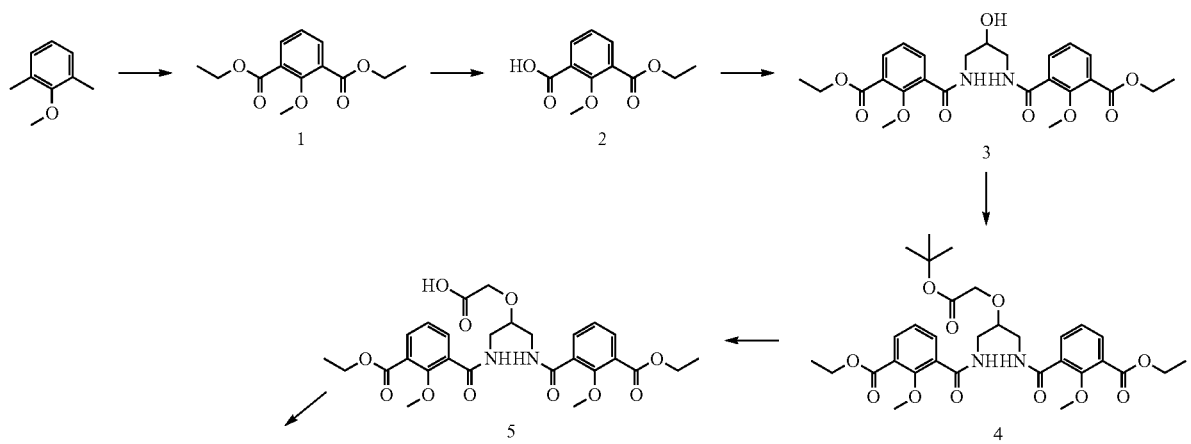

-continued

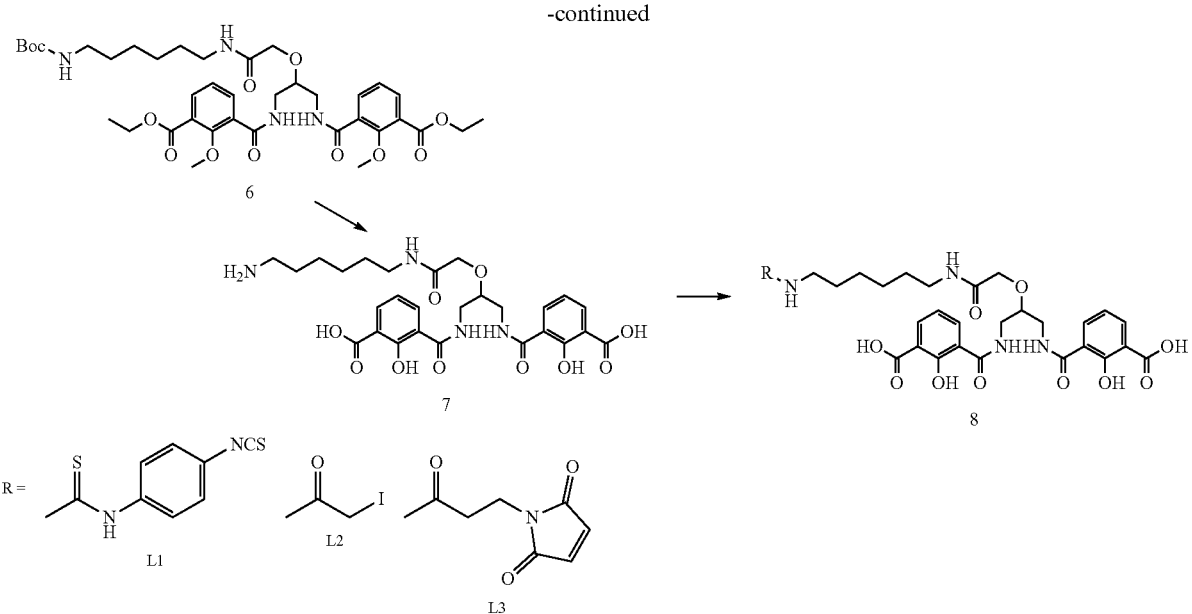

Compound 1 was obtained in two steps by oxidation of 2,6-dimethyl anisole by $KMnO_4$ in the presence of NaOH at 110° C. overnight, followed by acidification of the medium and esterification in the presence of EtOH. The overall yield was 79% for the two steps.

TLC: $R_f$=0.84 (SiOH, DCM/MeOH: 95/5). $^1$H-NMR (400 MHz, $CDCl_3$) δ 1.36 (t, J=7.0 Hz, 6H, $CH_3$), 3.90 (s, 3H, $CH_3$), 4.35 (q, J=7.1 Hz, 4H, $CH_2$), 7.16 (t, J=7.8 Hz, 1H, $H_{ar}$), 7.87 (d, J=7.8 Hz, 2H, $H_{ar}$). $^{13}$C-NMR (100 MHz, $CDCl_3$) δ 14 ($CH_3$), 61 ($CH_2$), 64 ($CH_3$), 123 (CH), 127 ($C_{quat}$), 135 (CH), 159 ($C_{quat}$), 166 ($C_{quat}$). ESI/MS (positive mode): m/z=253.11 ([M+H]$^+$, 100%), 254.11 ([M+H]$^+$, 13%), 255.11 ([M+H]$^+$, 2%), 527.19 ([2 M+Na$^+$], 48%). Elemental analysis calculated for $C_{13}H_{16}O_5$·⅓$H_2O$: C, 60.46, H, 6.50. Found: C, 60.63, H, 6.29.

Compound 2 was obtained by a controlled saponification of compound 1 by KOH in EtOH with a yield of 76%.

TLC: $R_f$=0.70 (SiOH, DCM/MeOH: 9/1). $^1$H-NMR (400 MHz, $CDCl_3$) δ 1.42 (t, J=7.1 Hz, 3H, $CH_3$), 4.05 (s, 3H, $CH_3$), 4.43 (q, J=7.1 Hz, 2H, $CH_2$), 7.3 (t, J=7.8 Hz, 1H, $H_{ar}$), 8.08 (dd, J=7.8 Hz, 1.9 Hz, 1H, $H_{ar}$), 8.30 (dd, J=7.8 Hz, 1.8 Hz, 1H, $H_{ar}$).

Compound 3 was obtained by peptidic coupling of compound 2 with 1,3-diamino-2-propanol using EDCI and HOBt in acetonitrile and in the presence of triethylamine with 74% yield.

TLC: $R_f$=0.51 (SiOH, DCM/MeOH: 95/5). $^1$H-NMR (400 MHz, $CDCl_3$) δ 1.42 (t, J=7.1 Hz, 6H, $CH_3$), 3.53-3.60 (m, 2H, $CH_2$), 3.69-3.76 (m, 2H, $CH_2$), 4.00 (s, 6H, $CH_3$), 4.02-4.06 (m, 1H, CH), 4.25 (d, J=4.1 Hz, 1H, OH), 4.41 (q, J=7.1 Hz, 4H, $CH_2$), 7.27 (t, J=7.7 Hz, 2H, $H_{ar}$), 7.93 (dd, J=7.7 Hz, 1.9 Hz, 2H, $H_{ar}$), 8.23 (dd, J=7.9 Hz, 1.9 Hz, 2H, $H_{ar}$), 8.36 (t, J=5.9 Hz, 2H, NH). $^{13}$C-NMR (100 MHz, $CDCl_3$) δ 14 ($CH_3$), 44 ($CH_2$), 62 ($CH_2$), 64 ($CH_3$), 72 (CH), 124 (CH), 126 ($C_{quat}$), 127 ($C_{quat}$), 135 (CH), 136 (CH), 158 ($C_{quat}$), 166 ($C_{quat}$), 166 ($C_{quat}$). IR (cm$^{-1}$, ATR) v 3376, 2940, 1723, 1642, 1525, 1417, 1255, 1131. ESI/MS (positive mode): m/z=503.20 ([M+H]$^+$, 100%), 504.20 ([M+H]$^+$, 21%), 505.20 ([M+H]$^+$, 3%), 1027.33 ([2 M+Na$^+$], 27%). Elemental analysis calculated for $C_{25}H_{30}N_2O_9$, 1$H_2O$: C, 57.69, H, 6.20, N, 5.38. Found: C, 57.88, H, 5.89, N, 5.85.

Compound 4 was obtained by a Williamson type nucleophilic substitution using compound 3, potassium t-butanoate and t-butylbromoacetate in THF at 78° C. for one hour with 51% yield after purification.

TLC: $R_f$=0.66 (SiOH, DCM/MeOH: 95/5). $^1$H-NMR (400 MHz, $CDCl_3$) δ 1.42 (t, J=7.2 Hz, 6H, $CH_3$), 1.47 (s, 9H, $CH_3$), 3.46-3.52 (m, 2H, $CH_2$), 3.77-3.82 (m, 1H, CH), 3.84-3.92 (m, 2H, $CH_2$), 3.98 (s, 6H, $CH_3$), 4.16 (s, 2H, $CH_2$), 4.41 (q, J=7.2 Hz, 4H, $CH_2$), 7.25 (t, J=7.8 Hz, 2H, NH), 7.91 (dd, J=7.4 Hz, 1.9 Hz, 2H, $H_{ar}$), 8.20 (dd, J=8.0 Hz, 1.6 Hz, 2H, $H_{ar}$), 8.40 (t, J=5.8 Hz, 2H, $H_{ar}$). $^{13}$C-NMR (100 MHz, $CDCl_3$) δ 14 ($CH_3$), 28 ($CH_3$), 40 ($CH_2$), 61 ($CH_2$), 64 ($CH_3$), 68 (CH), 78 ($CH_2$), 82 ($C_{quat}$), 124 (CH), 126 ($C_{quat}$), 128 ($C_{quat}$), 135 (CH), 136 (CH), 158 ($C_{quat}$), 165 ($C_{quat}$), 166 ($C_{quat}$), 170 ($C_{quat}$). IR (cm$^{-1}$, ATR) v 3376, 2980, 1725, 1653, 1518, 1417, 1255, 1125, 994. ESI/MS (positive mode): m/z=617.27 ([M+H$^+$], 100%), 618.27 ([M+H$^+$], 35%), 619.27 ([M+H$^+$], 9%), 620.28 ([M+H$^+$], 1%). Elemental analysis calculated for $C_{31}H_{40}N_2O_{11}$: C, 60.38, H, 6.54, N, 4.83. Found: C, 60.69, H, 6.53, N, 4.83.

Compound 5 was obtained by deprotection of the t-butyl ester group using trifluoroacetic acid in dichloromethane at 50° C. with 70% yield.

TLC: $R_f$=0.37 (SiOH, DCM/MeOH: 95/5). $^1$H-NMR (400 MHz, $CDCl_3$) δ 1.37 (t, J=7.1 Hz, 6H, $CH_3$), 3.50-3.54 (m, 2H, $CH_2$), 3.78-3.82 (m, 3H, CH; $CH_2$), 3.91 (s, 6H, $CH_3$), 4.27 (s, 2H, $CH_2$), 4.36 (q, J=7.2 Hz, 4H, $CH_2$), 7.21 (t, J=7.7 Hz, 2H, $H_{ar}$), 7.88 (dd, J=7.7 Hz, 1.6 Hz, 2H, $H_{ar}$), 8.14 (dd, J=7.8 Hz, 1.6 Hz, 2H, $H_{ar}$), 8.49 (t, J=5.5 Hz, 2H, NH). $^{13}$C-NMR (100 MHz, $CDCl_3$) δ 14 ($CH_3$), 40 ($CH_2$), 62 ($CH_2$), 64 ($CH_3$), 67 (CH), 78 ($CH_2$), 124 (CH), 126 ($C_{quat}$), 128 ($C_{quat}$), 135 (CH), 136 (CH), 158 ($C_{quat}$), 165 ($C_{quat}$), 166 ($C_{quat}$), 173 ($C_{quat}$, $C_{15}$). IR (cm$^{-1}$, ATR) v 3370, 2982, 2941, 1722, 1646, 1525, 1417, 1257, 1130, 992. ESI/MS (positive mode): m/z=561.21 ([M+H$^+$], 100%), 562.21 ([M+H$^+$], 27%), 563.21 ([M+H$^+$], 7%), 564.21 ([M+H$^+$], 1%), 1143.39 ([2 M+Na$^+$], 97%). Elemental analysis calculated for $C_{27}H_{32}N_2O_{11}$·$CH_3OH$: C, 56.75, H, 6.12, N, 4.73. Found: C, 57.09, H, 5.93, N, 5.13.

Compound 6 was obtained by a peptidic coupling between 5 and t-butyl-6-aminohexylcarbamate using EDCI and HOBt in acetonitrile at 0° C. with 61% yield.

TLC: $R_f$=0.69 (SiOH, DCM/MeOH: 9/1). $^1$H-NMR (400 MHz, CDCl$_3$) δ 1.29-1.30 (m, 4H, CH$_2$), 1.40-1.42 (m, 17H, CH$_3$; CH$_2$; CH$_3$), 1.47-1.53 (m, 2H, CH$_2$), 3.06 (q, J=3.06 Hz, 2H, CH$_2$), 3.25 (q, J=6.7 Hz, 2H, CH$_2$), 3.68-3.74 (m, 5H, CH; CH$_2$; CH$_2$), 3.95 (s, 6H, CH$_3$), 4.11 (s, 2H, CH$_2$), 4.40 (q, J=7.1 Hz, 4H, CH$_2$), 4.58 (s, 1H, NH), 7.07 (t, J=5.6 Hz, 1H, NH), 7.27 (t, J=7.8 Hz, 2H, H$_{ar}$), 7.93 (dd, J=7.7 Hz, 1.7 Hz, 2H, H$_{ar}$), 8.20-8.22 (m, 2H, H$_{ar}$), 8.26 (t, J=6.0 Hz, 2H, NH). $^{13}$C-NMR (100 MHz, CDCl$_3$) δ 14 (CH$_3$), 26 (CH$_2$), 27 (CH$_2$), 29 (CH$_3$), 30 (CH$_2$), 30 (CH$_2$), 39 (CH$_2$), 40 (CH$_2$), 40 (CH$_2$), 62 (CH$_2$), 64 (CH$_2$), 70 (CH), 79 (CH$_2$), 124 (CH), 126 (C$_{quat}$), 128 (C$_{quat}$), 135 (CH), 136 (CH), 156 (C$_{quat}$), 158 (C$_{quat}$), 166 (C$_{quat}$), 166 (C$_{quat}$), 169 (C$_{quat}$). IR (cm$^{-1}$, ATR) ν 3334, 2977, 2934, 2859, 1710, 1650, 1521, 1461, 1254, 1131, 995. ESI/MS (positive mode): m/z=781.36 ([M+Na$^+$], 100%), 782.37 ([M+Na$^+$], 45%), 783.37 ([M+Na$^+$], 11%), 784.37 ([M+Na$^+$], 2%), 1539.73 ([2 M+Na$^+$], 29%). Elemental analysis calculated for C$_{38}$H$_{54}$N$_4$O$_{12}$: C, 60.14, H, 7.17, N, 7.38. Found: C, 59.79, H, 7.36, N, 7.62.

Compound 7 was obtained by deprotection of the protecting groups of compound 6 using BBr$_3$ in dichloromethane at −78° C., followed by saponification with NaOH in EtOH, with 80% yield for the two steps.

TLC: $R_f$=0.68 (C$_{18}$, H$_2$O (0.1% TFA/ACN (0.1% TFA): 8/2). $^1$H-NMR (400 MHz, D$_2$O) δ 1.05-1.15 (m, 4H, CH$_2$), 1.27 (m, J=7.2 Hz, 4H; CH$_2$), 2.51 (t, J=7.2 Hz, 2H, CH$_2$), 3.07 (t, J=7.1 Hz, 2H, CH$_2$), 3.63 (dd, J=14.4 Hz, 6.6 Hz, 2H, CH$_2$), 3.75 (dd, J=14.2 Hz, 4.2 Hz, 2H, CH$_2$), 3.91-3.95 (m, 1H, CH), 4.22 (s, 2H, CH$_2$), 6.63 (t, J=7.6 Hz, 2H, H$_{ar}$), 7.46-7.48 (m, 2H, H$_{ar}$), 7.85 (dd, J=7.8 Hz, 1.9 Hz, 2H, H$_{ar}$). $^{13}$C-NMR (100 MHz, D$_2$O) δ 26 (CH$_2$), 26 (CH$_2$), 28 (CH$_2$), 31 (CH$_2$), 39 (CH$_2$), 40 (CH$_2$), 40 (CH$_2$), 68 (CH$_2$), 78 (CH), 115 (CH), 119 (C$_{quat}$), 127 (C$_{quat}$), 132 (CH), 133 (CH), 164 (C$_{quat}$), 170 (C$_{quat}$), 172 (C$_{quat}$), 177 (C$_{quat}$). IR (cm$^{-1}$, ATR) ν 2940, 2857, 1660, 1592, 1540, 1433, 1256, 1190, 1157, 1130, 756. ESI/MS (positive mode): m/z=575.23 ([M+H$^+$], 100%), 576.24 ([M+H$^+$], 81%), 577.24 ([M+H$^+$], 30%), 578.24 ([M+H$^+$], 7%), 579.24 ([M+H$^+$], 2%). Elemental analysis calculated for C$_{27}$H$_{34}$N$_4$O$_{10}$·TFA·2H$_2$O: C, 51.77, H, 5.66, N, 8.63. Found: C, 51.40, H, 5.49, N, 8.34.

Ligand L1 was obtained with 88% yield by reaction of compound 7 with p-phenyl-bisisothiocyanate.

TLC: $R_f$=0.63 (C$_{18}$, H$_2$O (0.1% TFA/ACN)/(0.1% TFA): 6/4). $^1$H-NMR (400 MHz, DMSO) δ 1.20-1.27 (m, 4H, CH$_2$), 1.37 (m, J=6.9 Hz, 2H; CH$_2$), 1.48 (m, J=7.0 Hz, 2H, CH$_2$), 3.06 (q, J=6.5 Hz, 2H, CH$_2$), 3.42-3.48 (m, 4H, CH$_2$), 3.56-3.62 (m, 2H, CH$_2$), 3.71 (m, J=5.2 Hz, 1H, CH), 4.04 (s, 2H, CH$_2$), 6.99 (t, J=7.8 Hz, 2H, H$_{ar}$), 7.35-7.37 (m, 2H, H$_{ar}$), 7.55-7.57 (m, 2H, H$_{ar}$), 7.69 (t, J=5.9 Hz, 1H, NH), 7.94 (dd, J=7.8 Hz, 1.8 Hz, 2H, H$_{ar}$), 8.04 (dd, J=7.8 Hz, 1.8 Hz, 2H, H$_{ar}$), 8.76-8.78 (m, 2H, NH), 9.76 (s, 1H, NH). $^{13}$C-NMR (100 MHz, DMSO) δ 27 (CH$_2$), 29 (CH$_2$), 30 (CH$_2$), 39 (CH$_2$), 41 (CH$_2$), 44 (CH$_2$), 46 (CH$_2$), 69 (CH$_2$), 79 (CH), 116 (C$_{quat}$), 119 (CH), 121 (C$_{quat}$), 123 (CH), 125 (C$_{quat}$), 127 (CH), 133 (C$_{quat}$), 134 (CH), 136 (CH), 140 (C$_{quat}$), 161 (C$_{quat}$), 166 (C$_{quat}$), 170 (C$_{quat}$), 172 (C$_{quat}$), 181 (C$_{quat}$). IR (cm$^{-1}$, ATR) ν 3308, 2932, 2099, 1643, 1598, 1538, 1504, 1436, 1263, 1191, 1155, 759. HR-ESI/MS (positive mode): m/z=767.2177 ([M+H$^+$], 100%), 768.2203 ([M+H$^{+}$], 44%), 769.2246 ([M+H$^+$], 16%), 770.2179 ([M+H$^+$], 4%), 771.2116 ([M+H$^+$], 1%). Elemental analysis calculated for: C$_{35}$H$_{38}$N$_6$O$_{10}$S$_2$·H$_2$O: C, 53.56, H, 5.14, N, 10.71, S, 8.17. Found: C, 53.33, H, 5.05, N, 10.42, S, 8.15.

Ligand L2 was obtained with 57% yield by reaction of compound 7 with 2,5-dioxopyrrolidin-1-yl-2-iodoacetate in DMF in the presence of triethylamine.

Ligand L3 was obtained by reaction of 2,5-dioxopyrrolidin-1-yl-3-(2,5-dioxo-2,5-dihydro-1H-pyrrol-1-yl)propanoate and compound 7 in DMF containing N-methylmorpholine at room temperature with 53% yield.

Synthesis of the Ligand L4

The claimed ligand L4 was prepared by following the below synthesis steps and with the below intermediary compounds 1, 2, 10 and 11:

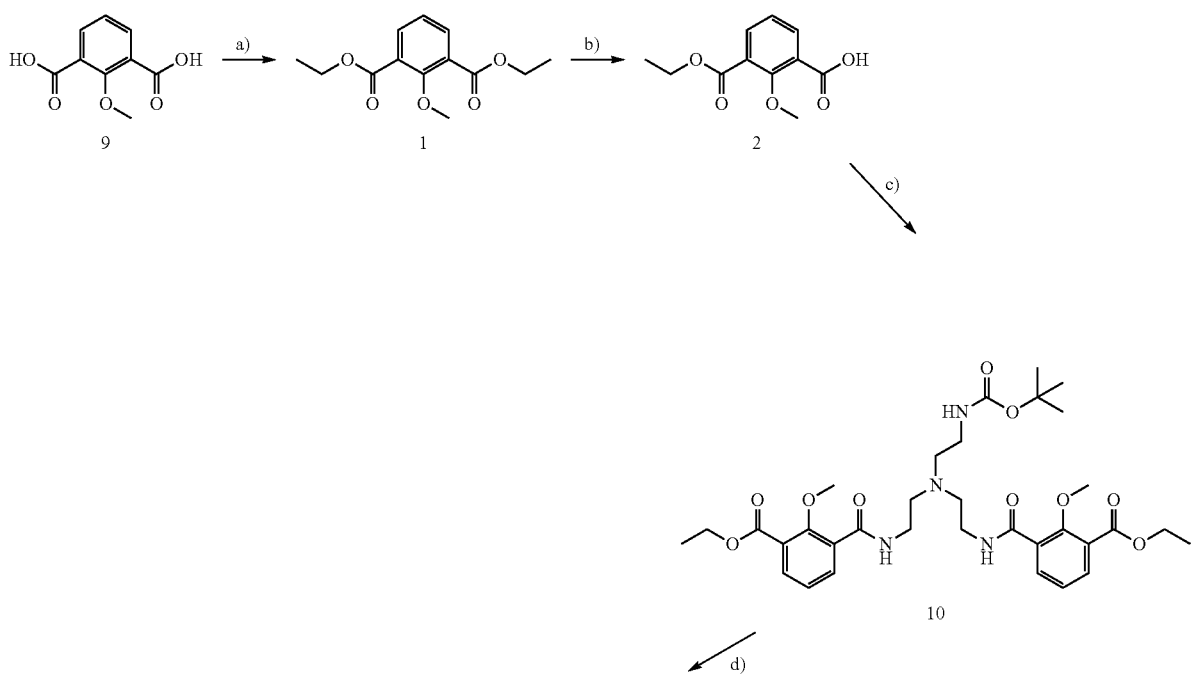

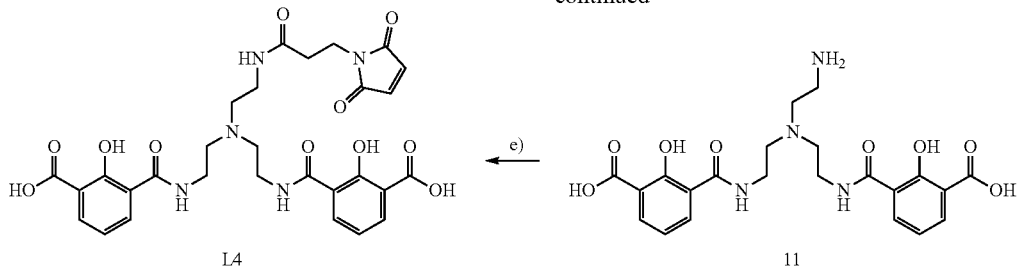

Compound 1 was obtained by esterification of compound 9 using SOCl₂ followed by evaporation of the excess of thionyl chloride and reaction with EtOH in the presence of Et₃N with an overall yield of 68%.

Compound 10 was obtained by peptidic coupling of compound 2 and t-butyl (2-(bis(2-aminoethyl)amino)ethyl) carbamate using EDCI and HOBt in acetonitrile containing triethylamine with 84% yield.

TLC: $R_f$=0.40 (SiOH, DCM/MeOH: 95/5). ¹H-NMR (300 MHz, CDCl₃) δ 1.33 (s, 9H, CH₃), 1.37 (t, J=7.2 Hz, 6H, CH₃), 2.69 (t, J=6 Hz, 2H, CH₂), 2.77 (t, J=6.2 Hz, 4H, CH₂), 3.18 (td, 2H, J=5.0 et 6.2 Hz, CH₂), 3.54 (q, J=6 Hz, 4H, CH₂), 3.85 (s, 6H, CH₃), 4.38 (q, J=7.2 Hz, 4H, CH₂), 7.19 (t, J=7.8 Hz, 2H, $H_{ar}$), 7.86 (dd, J=1.9 et 7.8 Hz, 2H, $H_{ar}$), 7.93 (t, J=5.0 Hz, 1H, NH), 8.09 (dd, J=1.9 et 7.8 Hz, 2H, $H_{ar}$). ¹³C-NMR (100 MHz, CDCl₃) δ 14 (CH₃), 28 (CH₃), 37 (CH₂), 38 (CH₂), 53 (CH₂), 61 (CH₂), 63 (CH₂), 78 ($C_{quat}$), 124 ($C_{quat}$), 125 ($C_{quat}$), 128 (CH), 134 (CH), 135 (CH), 155 ($C_{quat}$), 157 ($C_{quat}$), 164 ($C_{quat}$), 165 ($C_{quat}$). ESI/MS (positive mode): m/z=659.33 ([M+H⁺], 100%), 660.33 ([M+2H⁺], 40%), 661.33 ([M+3H⁺], 12%), 662.34 ([M+4H+], 4%). Elemental analysis calculated for C₃₃H₄₆N₄O₁₀·H₂O: C, 58.56, H, 7.15, N, 8.28. Found: C, 58.80, H, 6.89, N, 5.91.

Compound 11 was obtained in two steps using BBr₃ in CH₂Cl₂ at −78° C. followed by evaporation and saponification using NaOH in a water/methanol mixture with 60% overall yield.

TLC: $R_f$=0.30 (C₁₈, H₂O (0.1% TFA)/ACN (0.1% TFA): 8/2. ¹H-NMR (400 MHz, D₂O) δ 2.59 (m, 4H, CH₂), 2.72 (t, J=5.0 Hz, 4H, CH₂), 3.42 (t, J=5.0 Hz, 4H, CH₂), 6.43 (t, J=7.7 Hz, 2H, $H_{ar}$), 7.25 (dd, J=1.8 et 7.7 Hz, 2H, $H_{ar}$), 7.69 (dd, J=1.8 et 7.7 Hz, 2H, $H_{ar}$). ¹³C-NMR (100 MHz, D₂O) δ 37 (CH₂), 38 (CH₂), 51 (CH₂), 54 (CH₂), 117 ($C_{quat}$), 118 ($C_{quat}$), 119 (CH), 133 (CH), 134 (CH), 159 ($C_{quat}$), 167 ($C_{quat}$), 174 ($C_{quat}$). ESI/MS (positive mode): m/z=475.18 ([M+H⁺], 100%), 476.18 ([M+2H⁺], 28%), 477.18 ([M+3H+], 6%), 949.36 ([2 M], 6%).

Ligand L4 was obtained by reaction of compound 11 with N-Succinimidyl 3-maleimidopropionate in DMF containing Et₃N at 0° C., with 20% yield.

TLC: $R_f$=0.30 (C₁₈, H₂O (0.1% TFA)/ACN (0.1% TFA): 7/3. ¹H-NMR (400 MHz, D₂O) δ 2.35 (t, J=5.8 Hz, 2H, CH₂), 2.74 (t, J=6.5 Hz, 2H, CH₂), 2.83 (t, J=7.0 Hz, 4H, CH₂), 3.30 (t, J=5.8 Hz, 2H, CH₂), 3.35 (t, J=6.5 Hz, 2H, CH₂), 3.50 (t, J=7.0 Hz, 4H, CH₂), 5.97 (s, 2H, CH=CH), 6.48 (t, J=7.2 Hz, 2H, $H_{ar}$), 7.30 (d, J=7.2 Hz, 2H, $H_{ar}$), 7.75 (d, J=7.2 Hz, 2H, $H_{ar}$). ¹³C-NMR (100 MHz, CDCl₃) δ 22 (CH₂), 23 (CH₂), 23.5 (CH₂), 24 (CH₂), 39 (CH₂), 40 (CH₂), 99 ($C_{quat}$), 106 ($C_{quat}$), 111 (CH), 117 (CH), 119 (CH), 123 (CH=CH), 154 ($C_{quat}$), 158 ($C_{quat}$), 161 ($C_{quat}$), 162 ($C_{quat}$), 166 ($C_{quat}$).

Synthesis of the Ligand L5

The ligand L5 was prepared by following the below synthesis steps:

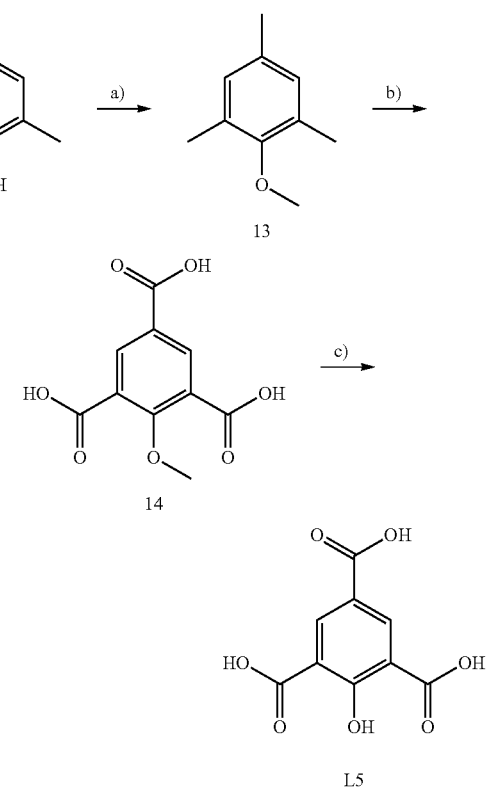

The synthesis of ligand L5 started, at step a, with the protection of the alcohol function of 2,4,6-trimethylphenol corresponding to compound 12 by a SN2 nucleophilic substitution in presence of methyl iodide (MeI) and potassium carbonate (K₂CO₃), with a yield of 97%.

The second step b was the oxidation of the three methyl groups of compound 13 obtained from step a, with KMnO₄ and KOH in H₂O. The yield of step b was 62%.

The last step c of the synthesis was the deprotection of the phenolate function of compound 14 by O-demethylation in the presence of a solution of HBr/AcOH (50/50). The ligand L5 was obtained by precipitation and centrifugation with a yield of 60%.

Synthesis of the Ligand L6

The ligand L6 was prepared by following the below synthesis steps:

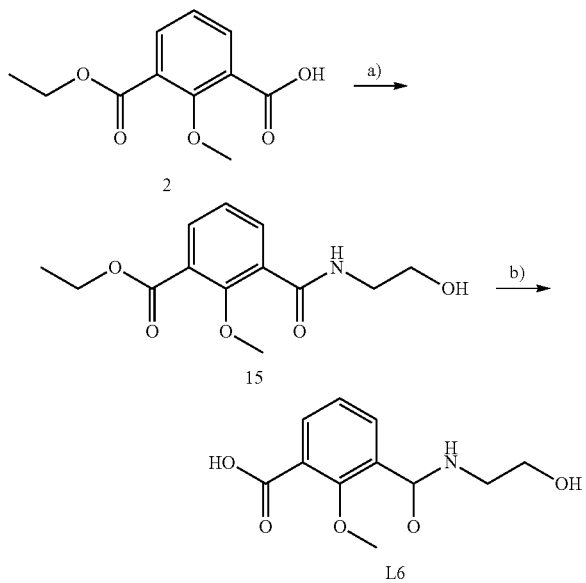

Compound 2 is solubilized in thionyl chloride. The solution is heated at 90° C. during 5 h. After evaporation, ethanolamine and distilled triethylamine are added. The crude product is extracted. After purification by FPLC using silica gel, compound 15 was obtained.

TLC: 0.3 (SiOH, DCM/MeOH); NMR¹H: (400 MHz, CDCl$_3$) δ 1.41 (t, J=7.1 Hz, 3H, CH$_3$), 3.64 (q, J=5.2 Hz, 2H, CH$_2$), 3.84 (t, J=5.1 Hz, 2H, CH$_2$), 3.91 (s, 3H, CH$_3$), 4.40 (q, J=7.1 Hz, 2H, CH$_2$), 7.27 (t, J=7.8 Hz, 1H, H$_{ar}$), 7.92 (dd, J=7.7 Hz, 1.9 Hz, 1H, H$_{ar}$), 8.17-8.21 (m, 1H, NH), 8.22 (dd, J=7.8 Hz, 1.9 Hz, 1H, H$_{ar}$). NMR¹³C: (100 MHz, CDCl$_3$) δ 14 (CH$_3$), 43 (CH$_2$), 62 (CH$_2$), 62 (CH$_2$), 64 (CH$_3$), 124 (CH), 126 (C$_{quat}$), 128 (C$_{quat}$), 135 (CH), 135 (CH), 158 (C$_{quat}$), 166 (C$_{quat}$), 166 (C$_{quat}$). ESI⁺/MS: m/z=268.12 ([M+H⁺], 82%), 557.21 ([2 M+H+]). Elemental analysis Calcd for C$_{13}$H$_{17}$NO$_5$, ⅓ H$_2$O: C, 57.14, H, 6.52, N, 5.13. Found: C, 57.14, H, 6.54, N, 5.14.

Compound 15 is solubilized in DCM with BBr$_3$. The crude product was dissolved in EtOH. NaOH was dissolved in 5 mL of H$_2$O. This basic solution was added to the mixture. The insoluble part was removed by filtration. Purification was performed by column chromatography to obtain the ligand L6.

TLC: 0.87 (C$_{18}$, H$_2$O/MeOH); NMR¹H: (400 MHz, H$_2$O+NaOD) δ 3.56 (t, J=5.6 Hz, 2H, CH$_2$), 3.77 (t, J=5.6 Hz, 2H, CH$_2$), 6.97 (t, J=7.6 Hz, 1H, H$_{ar}$), 7.90-7.98 (m, 2H, H$_{ar}$). NMR¹³C: (100 MHz, CDCl$_3$) 41 (CH$_2$), 61 (CH$_2$), 112 (CH), 119 (C$_{quat}$), 130 (CH), 131 (CH), 133 (C$_{quat}$), 166 (C$_{quat}$), 171 (C$_{quat}$), 179 (C$_{quat}$).

ESI⁻/MS: m/z=224.07 ([M−H+], 100%. Elemental analysis Calcd for C$_{10}$H$_{11}$NO$_5$, ¾ H$_2$O: C, 50.32, H, 5.28, N, 5.87. Found: C, 50.10, H, 4.97, N, 5.77.

Synthesis of the Ligand L7

The ligand L7 was prepared by following the below synthesis steps:

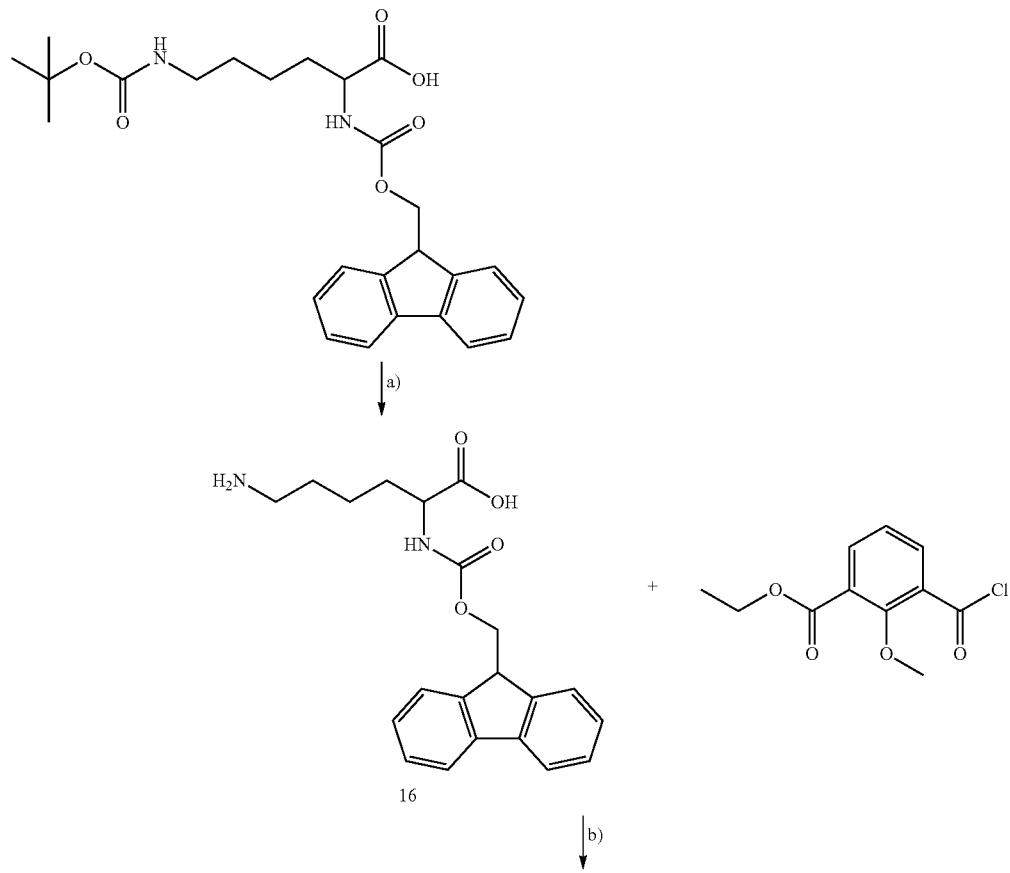

-continued
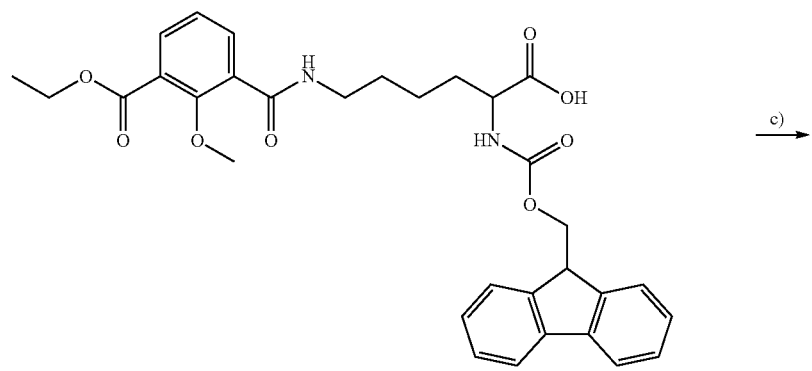
17
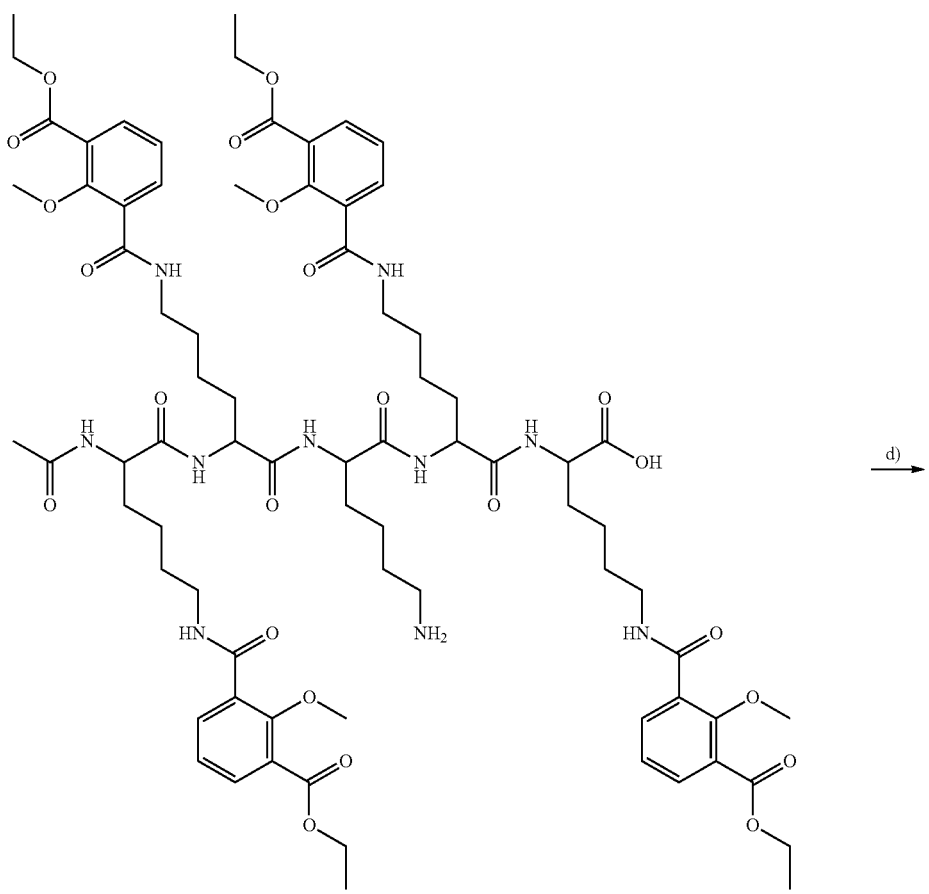
18

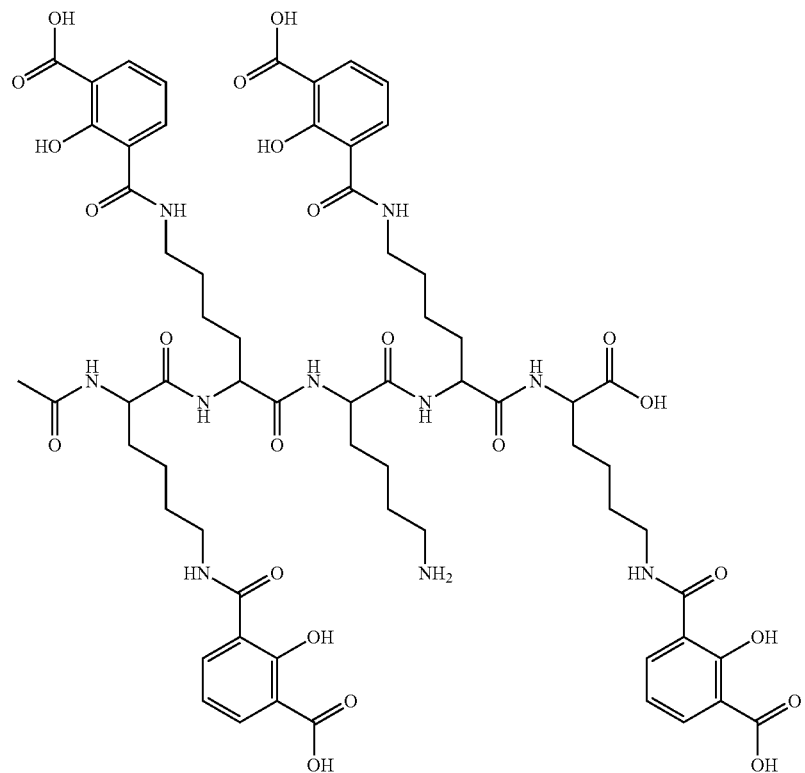

L7

Fmoc-Lys(Boc)-OH is solubilized in trifluoroacetic acid. The solution is stirred at room temperature overnight. The solution was evaporated under reduced pressure to afford compound 16.

NMR$^1$H: (400 MHz, MeOD) δ 1.42-1.53 (m, 2H), 1.61-1.77 (m, 3H), 1.86-1.95 (m, 1H), 2.92 (t, J=7.2 Hz, 2H, CH$_2$), 4.15-4.19 (m, 1H), 4.23 (t, J=6.9 Hz, 1H, CH), 4.32-4.36 (m, 1H), 4.39-4.44 (m, 1H), 7.29-7.33 (m, 2H, H$_{ar}$), 7.37-7.42 (in, 2H, H$_{ar}$), 7.65-7.70 (m, 2H, H$_{ar}$), 7.79-7.82 (2H, H$_{ar}$).

Compound 16 is solubilized in distilled THF (100 mL) with ethyl 3-(chlorocarbonyl)-2-methoxybenzoate and diisopropylethylamine. The reaction was quenched by H$_2$O (20 mL) and the solvent was evaporated under reduced pressure. Compound 17 was purified by column chromatography.

NMR$^1$H: (400 MHz, MeOD) δ 1.36 (t, J=7.2 Hz, 3H, CH$_3$), 1.48-1.82 (i, 5H), 1.86-1.97 (i, 1H), 3.41 (t, J=6.3 Hz, 2H, CH$_2$), 3.84 (s, 3H, CH$_3$), 4.15-4.22 (i, 2H), 4.28-4.40 (i, 4H), 7.21-7.31 (n, 3H, H$_{ar}$), 7.35-7.40 (m, 2H, H$_{ar}$), 7.64-7.69 (i, 2H, H$_{ar}$), 7.76-7.84 (4H, H$_{ar}$).

Compound 18 has been synthesised by solid support. Compound 18 was deprotected with BBr$_3$. The crude product was dissolved in EtOH. NaOH was dissolved in H$_2$O. This basic solution was added to the mixture. The insoluble part was removed by filtration. The filtrate was purified by column chromatography to afford compound L7.

ESI$^-$/MS high resolution: m/z=679.2808 ([M+2H+]/2, 100%), 1357.5484 ([M+H$^+$], 88%)

Synthesis of the Ligand L8

The ligand L8 was prepared by following the below synthesis steps:

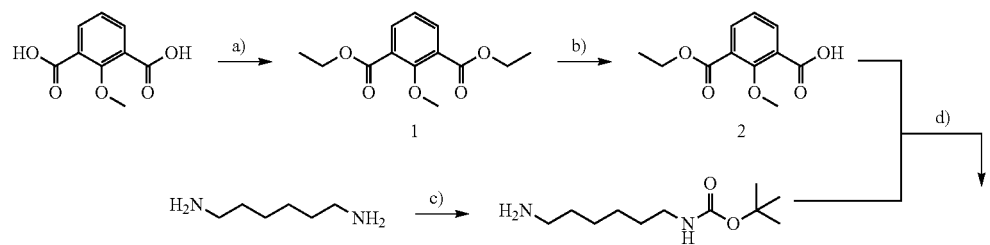

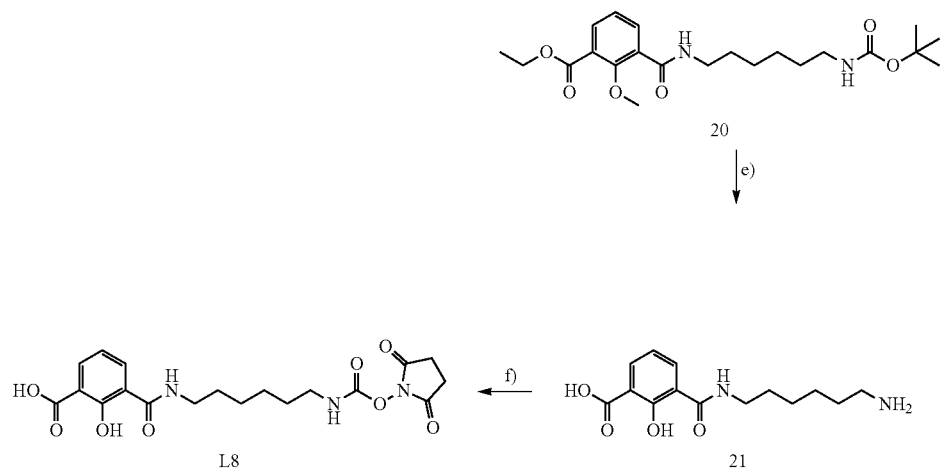

As previously, the carboxylic acids of 2-methoxyisophthalic acid have been activated by thionyl chloride and, after evaporation of the solvent, ethanol with triethylamine were added to form the diester 1.

$^1$H-NMR (300 MHz, CDCl$_3$) δ 7.87 (d, J=7.8 Hz, 2H), 7.16 (t, J=7.8 Hz, 1H), 4.35 (q, J=7.1 Hz, 4H), 3.89 (s, 3H), 1.36 (t, J=7.1 Hz, 6H).

$^{13}$C-NMR (75 MHz, CDCl$_3$) δ 165.7, 159.3, 134.7, 127.1, 123.4, 63.6, 61.3, 14.2. ESI$^+$/MS: m/z=253.11 ([M+H$^+$], 100), 254.11 ([M+H]$^+$, 130), 255.11 ([M+H]$^+$, 2%), 527.19 ([2 M+Na$^+$], 48%).

Elem. Anal. Calcd for C$_{13}$H$_{16}$O$_5$, ⅓H$_2$O: C, 60.46, H, 6.50. Found: C, 60.63, H, 6.29.

The second step is a classic saponification with a single equivalent of NaOH to get the monoacid 2 after extraction.

$^1$H-NMR (400 MHz, CDCl$_3$) δ 1.42 (t, J=7.1 Hz, 3H), 4.05 (s, 3H), 4.43 (q, J=7.1 Hz, 2H), 7.33 (t, J=7.8 Hz, 1H), 8.08 (dd, J=7.8 Hz, 1.9 Hz, 1H), 8.30 (dd, J=7.8 Hz, 1.8 Hz, 1H).

$^{13}$C-NMR (100 MHz, CDCl$_3$) δ 166.2, 165.3, 160.5, 137.4, 137.1, 126.7, 125.5, 124.3, 64.4, 62.1, 14.2.

ESI$^+$/MS: m/z=247.06 ([M+Na]$^+$, 100%), 248.06 ([M+Na]$^+$, 14%), 249.06 ([M+Na]$^+$, 2%), 471.12 ([2 M+Na$^+$], 47%).

Elem. Anal. Calcd for pour C$_{11}$H$_{12}$O$_5$: C, 58.93, H, 5.40. Found: C, 58.93, H, 5.44.

In parallel, the protection of a hexamethylenediamine linker was realized with di-tert-butyl dicarbonate to have a tert-butoxycarbonyl (BOC) group to get the compound 19.

$^1$H-NMR (300 MHz, CDCl$_3$) δ 4.64 (s, 1H), 3.08 (q, J=6.7 Hz, 2H), 2.65 (t, J=6.8 Hz, 2H), 1.46 (dd, J=10.2, 3.4 Hz, 4H), 1.41 (s, 9H), 1.30 (d, J=3.3 Hz, 4H), 1.15 (s, 2H).
$^{13}$C-NMR (75 MHz, CDCl$_3$) δ 155.9, 78.9, 42.0, 33.6, 30.0, 28.3, 26.59.

ESI$^+$/MS (H$_2$O+HCOOH): m/z 459.35 ([2 MNaH+H]$^+$, 100%).

Elem. Anal. Calcd for C$_{11}$H$_{24}$N$_2$O$_2$: C, 61.35; H, 10.77; N, 13.01. Found: C, 61.54; H, 9.01; N, 13.25. 1-Ethyl-3-(3-dimethylaminopropyl)carbodiimide (EDCI) and hydroxybenzotriazole (HOBt) have been added in a solution with the monoester 3-(ethoxycarbonyl)-2-methoxybenzoic acid (2) to activate the carboxyl function and to produce an amide bond with the protected linker (19). After purification, the compound 20 have been obtained.

$^1$H-NMR (300 MHz, CDCl$_3$) δ 8.18 (dd, J=7.8, 1.9 Hz, 1H), 7.88 (dd, J=7.7, 1.9 Hz, 1H), 7.75-7.65 (m, 1H), 7.23 (t, J=7.8 Hz, 1H), 4.65 (s, 1H), 4.37 (q, J=7.1 Hz, 2H), 3.86 (s, 3H), 3.43 (td, J=7.1, 5.7 Hz, 2H), 3.07 (q, J=6.7 Hz, 2H), 1.67-1.51 (m, 2H), 1.48-1.30 (m, 18H).

$^{13}$C-NMR (75 MHz, CDCl$_3$) δ 165.4, 164.6, 157.8, 155.9, 135.5, 134.2, 128.3, 125.5, 124.3, 78.9, 63.3, 61.3, 40.8, 39.6, 29.9, 29.4, 28.3, 26.6, 26.3, 14.1.

ESI$^+$/MS: m/z=423.25 ([M+H]$^+$, 100%); 424.25 ([M+H]$^+$, 20%); 425.25 ([M+H]$^+$, 5%); 845.48 ([2 M+H]$^+$, 45%).

Elem. Anal. Calcd for C$_{22}$H$_{34}$N$_2$O$_4$·0.5CH$_3$CN: C, 62.34; H, 8.08; N, 7.90. Found: C, 62.62; H, 7.71; N, 7.52.

For step e, the reaction to get compound 21 is the deprotection of the phenol and of the amine by BBr$_3$ followed by the deprotection of the ester by NaOH.

$^1$H-NMR (300 MHz, MeOD): δ 8.11 (dd, J=7.8, 1.7 Hz, 1H), 8.05 (dd, J=7.8, 1.7 Hz, 1H), 6.96 (t, J=7.7 Hz, 1H), 3.43 (t, J=6.9 Hz, 2H), 2.94 (t, J=7.5 Hz, 2H), 1.66 (m, 4H), 1.52-1.39 (m, 4H).

$^{13}$C-NMR (75 MHz, MeOD): δ 174.2, 167.6, 161.8, 137.1, 135.4, 121.6, 119.59, 117.0, 40.7, 40.5, 30.2, 28.4, 27.4, 27.0.

ESI$^+$/MS: m/z=281.15 ([M+H]$^+$, 100%); 282.15 ([M+H]$^+$, 18%); 283.16 ([M+H], 20%).

Elem. Anal. Calcd for C$_{14}$H$_{20}$N$_2$O$_4$·0.5D$_2$O·0.5 MeOD: C, 56.79; H, 6.90; N, 9.13. Found: C, 56.90; H, 6.52; N, 9.20.

With free carboxylic acids and free amines on the product 21, the activation of amine on the linker is necessary to promote thereafter the coupling. The choice is to use N,N'-disuccinimidyl carbonate to change the primary amine to an activated carbamate L8.

$^1$H-NMR (300 MHz, MeOD): δ 8.16 (dd, J=7.8, 1.8 Hz, 1H), 8.05 (dd, J=7.8, 1.8 Hz, 1H), 7.95 (t, J=5.6 Hz, 1H), 7.03 (t, J=7.8 Hz, 1H), 3.44 (t, J=6.9 Hz, 2H), 3.20 (m, 2H), 2.80 (s, 4H), 1.62 (m, 4H), 1.44 (m, 4H).

$^{13}$C-NMR (75 MHz, MeOD): δ 173.6, 172.6, 167.1, 161.3, 154.0, 137.9, 135.3, 122.1, 120.2, 115.0, 56.8, 42.5, 40.7, 30.3, 27.6, 27.3, 26.4.

ESI$^+$/MS: m/z=422.16 ([M+H]$^+$, 100%); 423.16 ([M+H]$^+$, 24%); 424.16 ([M+H]$^+$, 5%).

Elem. Anal. C$_{19}$H$_{23}$N$_3$O$_8$·0.5Et$_3$N$^+$Cl$^-$: C, 56.10; H, 5.98; N, 9.54. Found: C, 56.10; H, 5.96; N, 10.12.

Synthesis of the Ligand L9

The ligand L9 was prepared by following the below synthesis steps:

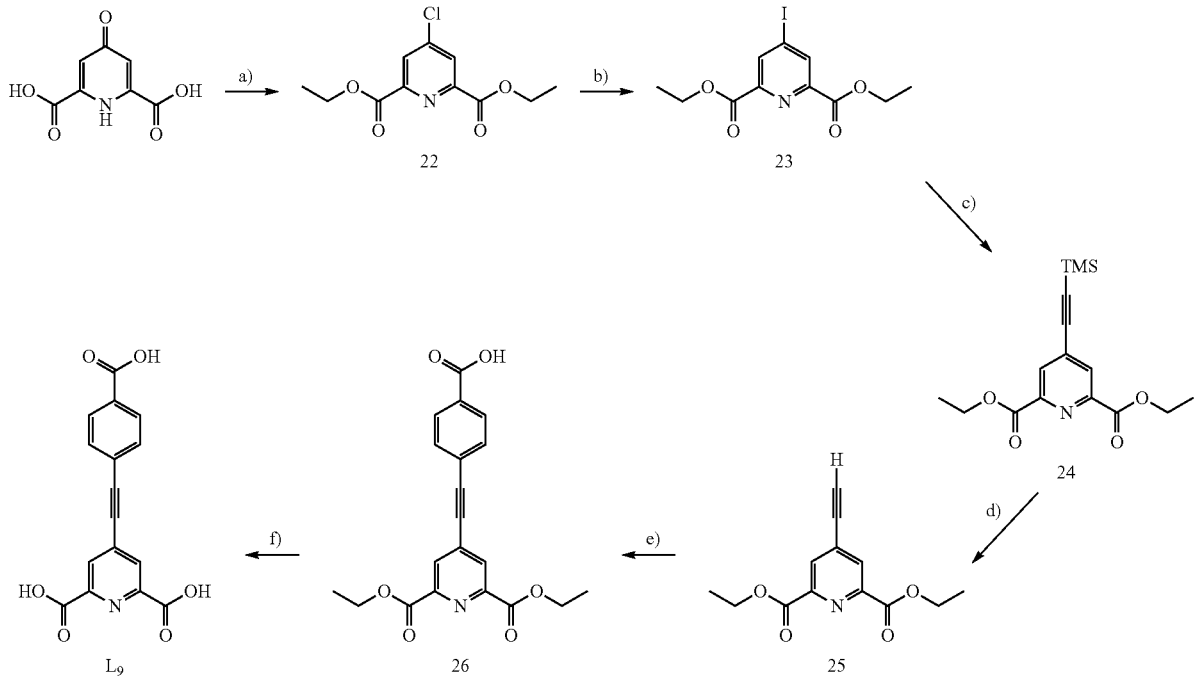

Starting from chelidamic acid, the first step of the synthesis is to activate the carboxylic acids by the method of Robison using and the 4-oxo position by thionyl chloride and to esterify with EtOH to form diethyl 4-chloropyridine-2,6-dicarboxylate (22). $^1$H-NMR (400 MHz, CDCl$_3$): δ 8.24 (s, 2H), 4.47 (q, J=6.8 Hz, 4H), 1.43 (t, J=6.8 Hz, 6H).

$^{13}$C-NMR (101 MHz, CDCl$_3$): δ 163.6, 149.7, 146.6, 128.1, 63.3, 14.2.

The chloride is substituted by an iodide (23) in the presence of a large quantity of sodium iodide and acetyl chloride under ultrasounds.

$^1$H-NMR (400 MHz, CDCl$_3$): δ 8.52 (s, 2H), 4.35 (q, J=7.2 Hz, 4H), 1.32 (t, J=7.2 Hz, 6H).

HRMS (MALDI-TOF): m/z=349.66 ([M+H]$^+$), 371.63 ([M+Na]$^+$), 720.79 ([2 M+Na]$^+$).

A Sonogashira coupling is used to add an acetylene group to the structure (24) with tetrakis(triphenylphosphine)palladium(0), copper(I) iodide, triethylamine and trimethylsilylacetylene (TMS-acetylene).

$^1$H-NMR (400 MHz, CDCl$_3$): δ 8.23 (s, 2H), 4.47 (q, J=7.2 Hz, 4H), 1.43 (t, J=7.2 Hz, 6H), 0.27 (s, 9H).

$^{13}$C-NMR (101 MHz, CDCl$_3$): δ 164.6, 149.2, 134.4, 130.2, 103.7, 100.9, 62.9, 14.6, 0.0.

HRMS (MALDI-TOF): m/z=320.07 ([M+H]$^+$).

After purification, the trimethylsilyl group can be deprotected by tetra-N-butylammonium fluoride (TBAF) in THF to get compound 25.

$^1$H-NMR (400 MHz, CDCl$_3$): δ 8.27 (s, 2H), 4.47 (q, J=7.1 Hz, 4H), 3.48 (s, 1H), 1.43 (t, J=7.1 Hz, 6H)

HRMS (MALDI-TOF): m/z=248.00 ([M+H]$^+$).

Compound 26 is obtained by a Sonogashira coupling between compound 25 and 4-iodobenzoic acid.

$^1$H-NMR (400 MHz, CDCl$_3$): δ 8.29 (s, 2H), 7.37 (d, J=8.4 Hz, 2H), 6.65 (d, J=8.4 Hz, 2H), 4.11 (q, J=7.1 Hz, 4H), 1.24 (t, J=7.1 Hz, 6H).

HRMS (MALDI-TOF): m/z=367.39 ([M+H]$^+$), 389.96 ([M+Na]$^+$).

The last step of the synthesis is the saponification of the esters with NaOH to yield ligand L9.

$^1$H-NMR (400 MHz, D$_2$O): δ 8.08 (s, 2H), 7.86 (d, J=8.3 Hz, 2H), 7.68 (d, J=8.3 Hz, 2H).

$^{13}$C-NMR (101 MHz, D$_2$O): δ 174.8, 169.3, 152.9, 136.9, 133.2, 131.7, 128.8, 126.7, 123.9, 98.8, 84.2.

HRMS (MALDI-TOF): m/z=311.94 ([M+H]$^+$).

Bio-Functionalization of Ligand L1 by Streptavidin:

Streptavidin is a tetrameric protein which has a very strong affinity with biotin. This strong interaction, often used in biotechnologies, represents a typical example of biological strong interaction as the interactions between antigen and antibody can be.

In this example, ligand L1 was used to label streptavidin, with the aim to produce ultrabright luminescent nanoparticles able to fix biotin.

Streptavidin was marked at room temperature in buffered aqueous solution in presence of 10 equivalents of compound L1. The marked streptavidin was purified by centrifugation on size exclusion filter (form Millipore, cut-off 10 kDa). The labeling rate of streptavidin (number of ligands L1 by streptavidin) was determined by UV-Visible absorption where the spectrum of marked streptavidin was deconvoluted as being a linear combination of the spectrum of streptavidin alone and of ligand L1. A labeling rate of 2.1 ligands by streptavidin was obtained.

Bio-Functionalization of Ligand L1 by Matuzumab Antibody:

Matuzumab antibody is a human monoclonal antibody which specifically recognizes the epidermal growth factor receptors (EGFR) overexpressed in some cancers (lungs, esophagus, stomach . . . ). Luminescent nanoparticles marked by Matuzumab could be used for luminescence microscopy imaging of epidermal growth factor receptors or for the detection thereof in solution by fluoro-immunology.

In this example, ligand L1 was used to label Matuzumab antibody, with the aim to produce ultrabright luminescent nanoparticles able to fix epidermal growth factor receptors.

13.2 µL of a 3.23 mM ligand L1 solution in DMSO were added to 10.4 µL of a Matuzumab containing solution at 1 mg·mL-1 (128 µM) and 176 µL of pH 9.0 carbonate buffer (ratio L1/Matuzumab=32/1). The sample was mixed, disposed in an aluminum sheet, then incubated 4 h 30 at room temperature with regular agitation. After purification by ultracentrifugation, elution and rinsing with a pH 8.04 TRIS/HCl buffer, a final solution with a volume of 80 µL was obtained. The final solution was diluted five times with the TRIS/HCl buffer.

The antibody and ligand concentrations were determined by UV-Visible absorption spectroscopy. An antibody concentration of 1.49 µM and a labeling ratio of 2.9-3.0 ligands by antibody were obtained.

Bio-Functionalization of Ligand L8 by Peptide KLVFF:

Peptide KLVFF is the sequence of amino acids which is responsible for the formation of amyloid fibers. This peptide was chosen because it is found in area that will fold into β-sheets, characteristic structure of amyloid fiber in formation and that will give a better interaction with the synapse. Knowing that these β-amyloid fibers aggregate significantly in the hippocampus, the idea is to specifically target these fibers with peptide KLVFF to make an early diagnosis of Alzheimer's disease.

In this example, the peptide KLVFF has been coupled with the ligand L8 with the aim to produce ultrabright luminescent nanoparticles able to fix β-amyloid fibers.

The peptide KLVFF (37 mg, $5.67 \times 10^{-5}$ mol) was dissolved in 1 mL of DMSO and 45 µL od DIPEA and L8 (41 mg, $9.73 \times 10^{-5}$ mol) was added in the solution. The reaction mixture was stirred at r.t. overnight. The solution was directly purified by column chromatography over Cis (Water/MeOH gradient from 100 to 50/50).

Experimental Measurement Methods of Luminescence Spectroscopy

UV-Vis absorption spectra were recorded in 1 cm optical path quartz suprasil cells (Hellma), using a PerkinElmer lambda 950 spectrometer or a Specord spectrometer from Jena Analytics.

Luminescence spectra were recorded on a FLP920 Edinburgh Instrument spectrophotometer using a 450 W Xe lamp and a Hamamatzu R928 red photomultiplier. All spectra were corrected using instrumental functions furnished by the supplier. When necessary, a 399 nm high pass filter was used to remove second order artifacts.

Luminescence quantum yields were measured according to conventional procedures described in *Molecular Fluorescence: Principles and Applications*, 2nd ed.; Valeur, B., Berberan-Santos, M. N., Eds.; Wiley-VCH: Weinheim, 2013, with optically diluted solutions (optical density <0.05), using [Ru(bipy)$_3$Cl$_3$] in water ($\Phi$=0.04, Ishida, H. et al, *Coord. Chem. Rev.* 2010, 254 (21), 2449-2458) as reference for Eu containing nanoparticles, a bipyridine Tb complex, [TbL(H$_2$O)] in water ($\Phi$=0.31, Weibel, N. et al, *J. Am. Chem. Soc.* 2004, 126 (15), 4888-4896) as reference for Tb containing nanoparticles.

Estimated errors on quantum yields are ±15%.

Brightnesses are calculated as the product of the molar absorption coefficient (calculated by applying the Beer-Lambert law to the absorption spectra) at the excitation wavelength by the luminescence quantum yield.

Luminescence lifetimes were recorded on the same instrument in the MCS mode using a 100 W Xe flash lamp working at 10 Hz, the temporal window being at least five times longer than the longest excited state lifetime measured. Excitation and emission slits were typically set at 5 and 3 nm apertures. The excitation wavelength was chosen as a function of the ligand at the maximum of the excitation spectra of the nanoparticles in presence of the ligand. The acquisition was stopped when the maximum intensity reached 10,000 counts.

Estimated errors on lifetimes are ±10%.

In all experiments, 16 µL of a mother solution of nanoparticles were diluted with 1984 µL of 0.1 M TRIS/HCl buffer at pH 7.0. Diluted solutions of the nanoparticles were then titrated by addition of increasing amounts of $5 \times 10^{-4}$ M solutions of the ligands in the same buffer.

Experimental Results

As already announced, the invention provides exceptional results in term of excited-state lifetime.

Such advantageous results have been demonstrated by experimental measurements realized on several examples of nanoparticles according to the invention, following the measurement method described in details above.

The excited-state lifetimes in aqueous medium τ of those compounds were measured for the emission of europium ions at 695 nm, after an excitation at a wavelength of $\lambda_{exc}$=330 nm corresponding to the ligand L5 absorption.

The obtained results have been gathered in the below table 2:

TABLE 2

| Example Number | Lanthanide nanoparticle Composition | Ligands | Excited-state lifetime τ (in ms) with $\lambda_{emission}$ = 695 nm and $\lambda_{excitation}$ = 330 nm |
|---|---|---|---|
| 6 | $La_{0.14}Tb_{0.85}Eu_{0.01}F_3$ | L5 | $\tau_1$ = 2.74 (6%) $\tau_2$ = 9.56 (94%) |
| 7 | $Tb_{0.99}Eu_{0.01}F_3$ | L5 | $\tau_1$ = 1.00 (3%) $\tau_2$ = 3.82 (15%) $\tau_3$ = 8.56 (82%) |
| 8 | $La_{0.1}Tb_{0.85}Eu_{0.05}F_3$ | L5 | $\tau_1$ = 1.49 (16%) $\tau_2$ = 7.06 (84%) |
| 9 | $La_{0.125}Tb_{0.85}Eu_{0.025}F_3$ | L5 | $\tau_1$ = 1.29 (10%) $\tau_2$ = 8.36 (90%) |
| 10 | $La_{0.14}Tb_{0.85}Eu_{0.01}F_3$ | L5 | $\tau_1$ = 1.43 (4%) $\tau_2$ = 9.10 (96%) |
| 11 | $La_{0.145}Tb_{0.85}Eu_{0.005}F_3$ | L5 | $\tau_1$ = 2.44 (6%) $\tau_2$ = 9.60 (94%) |
| 12 | $La_{0.1475}Tb_{0.85}Eu_{0.0025}F_3$ | L5 | $\tau_1$ = 2.63 (6%) $\tau_2$ = 10.02 (94%) |

For each measured example compound, the longest measured excited-state lifetime ($\tau_2$ or $\tau_3$) corresponds to the emission of the europium ions present in the core of the nanoparticle that are the most numerous, whereas the shortest one ($\tau_1$) correspond to the emission of the less numerous europium ions present at the surface of the core of the nanoparticle.

As can be observed, the longest measured excited-state lifetime ($\tau_2$ or $\tau_3$) is always considerably above the announced value of 3 ms or 5 ms, and is even superior to the preferred value 7 ms. It is thus considerably above the excited-state lifetimes described in prior art.

Further, and as never obtained in prior art, these exceptionally long excited-state lifetime measured values are very close to the theoretical value of radiative lifetime of europium which is a theoretical value, calculated for each element, that constitutes the maximal reachable value for the excited-state lifetime of this element.

For europium aqueous ions, this radiative lifetime theoretical value corresponds to 9.7 ms, as disclosed in prior art by Bünzli, J. C. G. Chem. Rev. 2010, 110, 2731.

Furthermore, this exceptionally long excited-state lifetime of nanoparticles according to the invention is not obtained at the expense of the brightness of the nanoparticles. Indeed, important brightness values were also measured for the compounds according to the invention, following the measurement method described in details above.

The measured brightness results have been gathered in the below table 3:

TABLE 3

| Example Number | Lanthanide nanoparticle Composition | Ligands | Brightness (in $M^{-1} \cdot cm^{-1}$) |
|---|---|---|---|
| 6 | $La_{0.14}Tb_{0.85}Eu_{0.01}F_3$ | L5 | $4.68 \times 10^7$ |
| 7 | $Tb_{0.99}Eu_{0.01}F_3$ | L5 | $1.08 \times 10^9$ |

Again, the measured values shows that the nanoparticles according to the invention have a brightness that is considerably above the announced value of $10^4$ $M^{-1} \cdot cm^{-1}$ (with at least 3 magnitude orders) or of $10^5$ $M^{-1} \cdot cm^{-1}$, and is even superior to the preferred value $10^6$ $M^{-1} \cdot cm^{-1}$, and that is thus largely better than the brightness of lanthanide based labels disclosed in prior art.

As above demonstrated, the luminescent lanthanide nanoparticles according to the invention provides a very effective solution to the technical problem, well beyond those proposed in prior art.

Obviously, the invention is not limited to the preferred embodiments described above and shown in the various figures, a person skilled in the art being able to make numerous modifications and imagine other embodiments without going beyond the framework and scope of the invention as defined in the appended claims.

What is claimed is:

1. A luminescent lanthanide nanoparticle, comprising a lanthanide ion nanoparticle including terbium, and several molecules of chromophore ligand that are bonded to the surface of the lanthanide ion nanoparticle,
   wherein said lanthanide ion nanoparticle comprises terbium ions and ions of at least a second lanthanide selected from the group consisting of: cerium, praseodymium, neodymium, samarium, europium, dysprosium, holmium, erbium, thulium and ytterbium;
   said ligand is an organic molecule comprising at least one chromophore radical of formula I or of formula II:

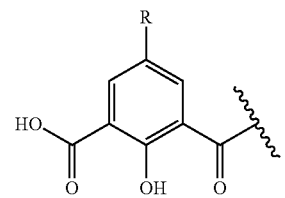

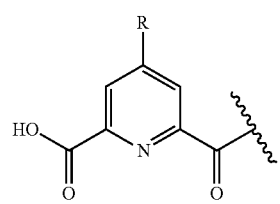

wherein R is selected from H, CN group or COOH group for formula I and wherein R is selected from CN group or COOH group for formula II,
wherein the luminescent lanthanide nanoparticle has an excited-state lifetime and a brightness that are simultaneously superior to 3 ms and $10^4$ $M^{-1} \cdot cm^{-1}$ respectively.

2. The luminescent lanthanide nanoparticle according to claim 1, wherein the ions of the second lanthanide are selected from europium, samarium, dysprosium and ytterbium.

3. The luminescent lanthanide nanoparticle according to claim 1, wherein said lanthanide ion nanoparticle further comprises ions of a third lanthanide selected from lanthanum, lutetium and gadolinium.

4. The luminescent lanthanide nanoparticle according to claim 1, wherein said lanthanide ion nanoparticle contains between 10 and 99.9 mol. % of terbium ions, and between 0.1 and 90 mol. % of ions of the second lanthanide.

5. The luminescent lanthanide nanoparticle according to claim 3, wherein said lanthanide ion nanoparticle contains between 1 and 98.9 mol. % of terbium ions, between 0.1 and 20 mol. % of ions of the second lanthanide, and between 1 and 90.9 mol. % of ions of the third lanthanide.

6. The luminescent lanthanide nanoparticle according to claim 1, wherein said ligand comprises n chromophore radicals and a spacer group, wherein the spacer group is a heteroatom containing carbon chain that links together the chromophore radicals and wherein n is an integer from 1 to 10.

7. The luminescent lanthanide nanoparticle according to claim 1, wherein said ligand further comprises a grafting function able to be covalently linked to a carrier molecule of analytical interest.

8. The luminescent lanthanide nanoparticle according to claim 7, wherein the luminescent nanoparticle further comprises a carrier molecule of analytical interest covalently attached to at least one ligand molecule.

9. The luminescent lanthanide nanoparticle according to claim 7, wherein the carrier molecule of analytical interest is selected from the group consisting of: peptides, proteins, antibodies, antibody moieties, small molecules of molecular weight lower than 2000 $g \cdot mol^{-1}$, biotin, desthiobiotin, streptavidin and Matuzumab antibody.

10. The luminescent lanthanide nanoparticle according to claim 1, wherein said ligand is selected from molecules having a structure according to formula L1, L3, L4 and L5:

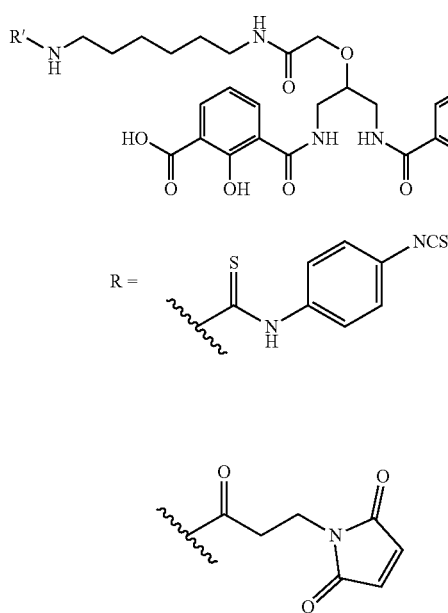

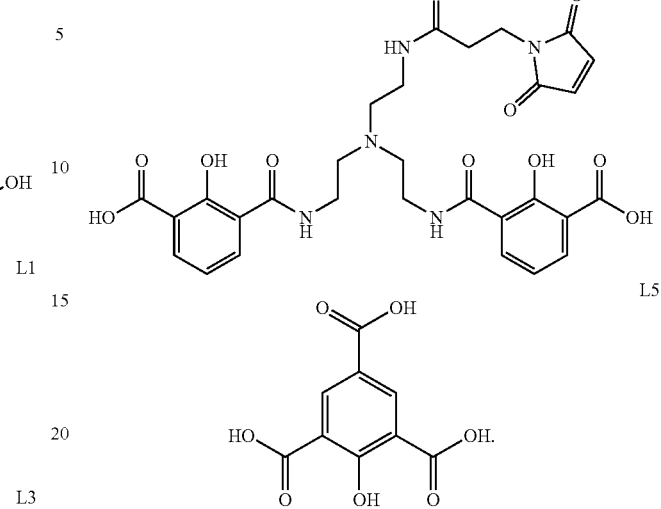

11. The luminescent lanthanide nanoparticle according to claim 1, wherein the luminescent lanthanide nanoparticle has a brightness and an excited-state lifetime that are simultaneously superior to 5 ms and $10^5$ $M^{-1} \cdot cm^{-1}$ respectively.

* * * * *